(12) United States Patent
Hierse et al.

(10) Patent No.: US 8,049,022 B2
(45) Date of Patent: Nov. 1, 2011

(54) FLUOROSURFACTANTS

(75) Inventors: Wolfgang Hierse, Gross-Zimmern (DE); Nikolai (Mykola) Ignatyev, Duisburg (DE); Martin Seidel, Darmstadt (DE); Elvira Montenegro, Weinheim (DE); Peer Kirsch, Yokohama Kanagawa (JP); Andreas Bathe, Darmstadt (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 200 days.

(21) Appl. No.: 12/307,145

(22) PCT Filed: Jul. 2, 2007

(86) PCT No.: PCT/EP2007/005840
§ 371 (c)(1),
(2), (4) Date: Dec. 31, 2008

(87) PCT Pub. No.: WO2008/003445
PCT Pub. Date: Jan. 10, 2008

(65) Prior Publication Data
US 2009/0312432 A1    Dec. 17, 2009

(30) Foreign Application Priority Data

Jul. 4, 2006 (DE) .......................... 10 2006 031 151

(51) Int. Cl.
*C07C 235/00* (2006.01)
*C11D 3/20* (2006.01)

(52) U.S. Cl. ................. 554/67; 554/35; 554/42; 554/61; 554/62; 554/66; 510/491; 510/490; 510/492; 510/501

(58) Field of Classification Search .......................... None
See application file for complete search history.

(56) References Cited

U.S. PATENT DOCUMENTS

| | | | |
|---|---|---|---|
| 1,985,424 | A | 12/1934 | Piggott |
| 2,703,798 | A | 3/1955 | Schwartz |
| 2,708,798 | A | 5/1955 | Warner et al. |
| 3,048,569 | A | 8/1962 | Harris |
| 3,311,599 | A | 3/1967 | Shumate |
| 3,359,319 | A | 12/1967 | Fawcett |
| 3,522,293 | A | 7/1970 | Furguson |
| 3,720,644 | A | 3/1973 | Haszeldine |
| 3,787,423 | A | 1/1974 | Bolhofer, et al. |
| 3,847,961 | A | 11/1974 | Koshar |
| 4,242,516 | A | 12/1980 | Mueller |
| 4,292,402 | A | 9/1981 | Pollet et al. |
| 4,324,741 | A | 4/1982 | Umemoto |
| 5,560,995 | A | 10/1996 | Usuki et al. |
| 5,691,299 | A | 11/1997 | Fabry |
| 6,110,976 | A | 8/2000 | Hansen et al. |
| 6,137,011 | A | 10/2000 | Marhold et al. |
| 6,175,041 | B1 | 1/2001 | Takasaki et al. |
| 6,582,849 | B1 | 6/2003 | Heider |
| 6,706,881 | B2 | 3/2004 | Damon et al. |
| 2004/0137385 | A1 | 7/2004 | Orem et al. |
| 2007/0135662 | A1 | 6/2007 | Nardello et al. |
| 2008/0149878 | A1 | 6/2008 | Kirsch et al. |
| 2009/0075594 | A1 | 3/2009 | Shichino et al. |
| 2009/0197201 | A1 | 8/2009 | Hierse et al. |
| 2009/0312432 | A1 | 12/2009 | Hierse et al. |
| 2009/0320718 | A1 | 12/2009 | Hierse et al. |
| 2010/0152081 | A1 | 6/2010 | Hierse et al. |

FOREIGN PATENT DOCUMENTS

| | | |
|---|---|---|
| DE | 691 26 789 | 2/1998 |
| DE | 199 08 943 | 9/2000 |
| DE | 199 41 566 | 3/2001 |
| DE | 102005000858 A1 | 7/2006 |
| EP | 0 015 592 | 9/1980 |
| EP | 0 558 515 | 9/1993 |
| EP | 1 081 129 | 3/2001 |
| EP | 1 228 062 | 8/2002 |
| EP | 1 296 182 | 3/2003 |
| EP | 1386920 | 2/2004 |
| GB | 809 060 | 2/1959 |
| JP | 56169666 | 12/1981 |
| JP | 57 108064 | 7/1982 |
| JP | 62 270555 | 11/1987 |
| JP | 1070444 | 3/1989 |
| JP | 6470443 | 3/1989 |

(Continued)

OTHER PUBLICATIONS

Dorwald, F. A., Side reactions in Organic Synthesis, 2005, Wiley: VCH, Weinheim pp. 1-15.*  Kanie, K, et al., A convenient synthesis of Trifluoromethyl Ethers by Oxidation Desulfurizatoin-Fluorination of Dithiocarbonates, 2000, Bull, Chem. Soc. Jpn, 73, 471-484 (14 pages).*

Kirsch, P., Modern Fluoroorganic Chemistry, 2004, Wiley VCHm pp. 67-72 & 144-145 (9 pages).*

Chwala, A. et al., "Handbuch der Textilhilfsmittel," Verlag Chemie, 1977.

Kennedy, G. L. et al., "The Toxicology of Perfluorooctanoate," Critical Reviews in Toxicology, 2004, vol. 34, No. 4, pp. 351-384.

Hildreth, James E. K., "N-D-Gluco-N-methylalkanamide compounds, a new class of non-ionic detergents for membrane biochemistry," Biochem. J., 1982, vol. 207, pp. 363-366.

(Continued)

*Primary Examiner* — Rosalynd Keys
*Assistant Examiner* — Yate K Cutliff
(74) *Attorney, Agent, or Firm* — Millen, White, Zelano & Branigan, P.C.

(57) ABSTRACT

The present invention relates to fatty acid alkanolamides or polyolamides containing at least one group Y, where Y stands for $CF_3-(CH_2)_a-O-$, $SF_5-$, $CF_3-(CH_2)_a-S-$, $CF_3CF_2S-$, $[CF_3-(CH_2)_a]_2N-$ or $[CF_3-(CH_2)_a]NH-$, where a stands for an integer selected from the range from 0 to 5, or formula (I), where Rf stands for $CF_3-(CH_2)_r-$, $CF_3-(CH_2)_r-O-$, $CF_3-(CH_2)_r-S-$, $CF_3CF_2-S-$, $SF_5-(CH_2)_r-$ or $[CF_3-(CH_2)_r]_2N-$, $[CF_3-(CH_2)_r]NH-$ or $(CF_3)_2N-(CH_2)_r-$, B stands for a single bond, O, NH, NR, $CH_2$, $C(O)-O$, $C(O)$, S, $CH_2-O$, $O-C(O)$, $N-C(O)$, $C(O)-N$, $O-C(O)-N$, $N-C(O)-N$, $O-SO_2$ or $SO_2-O$, R stands for alkyl having 1 to 4 C atoms, b stands for 0 or 1 and c stands for 0 or 1, q stands for 0 or 1, where at least one radical from b and q stands for 1, and r stands for 0, 1, 2, 3, 4 or 5, to processes for the preparation of these compounds, and to uses of these surface-active compounds.

23 Claims, No Drawings

FOREIGN PATENT DOCUMENTS

| | | |
|---|---|---|
| JP | 64070444 | 3/1989 |
| JP | 10-301379 | 11/1998 |
| JP | 2000 072735 | 3/2000 |
| JP | 2001 133984 A | 5/2001 |
| JP | 2001 294568 | 10/2001 |
| JP | 2003 267900 | 9/2003 |
| JP | 2005077961 | 3/2005 |
| WO | WO-92 06984 | 4/1992 |
| WO | WO-98 14540 | 4/1998 |
| WO | WO-99 19344 | 4/1999 |
| WO | WO-01 36410 | 5/2001 |
| WO | WO-2004 067692 | 8/2004 |
| WO | WO-2004 078990 | 9/2004 |
| WO | WO-2005 035472 | 4/2005 |
| WO | WO-03 010128 A2 | 2/2006 |
| WO | WO-2006 072401 | 7/2006 |
| WO | WO-2007 060839 | 5/2007 |
| WO | WO-2008 003447 | 1/2008 |

OTHER PUBLICATIONS

Abstract, Claims, and Background of the Invention for "Hair-treatment formulations." Retrieved from http://www.free-patent-search.net/Hair-Treatment/hair-treatment-71.htm on Jun. 20, 2006.

Knepper, Thomas P. et al., "Surfactants: Properties production, and environmental aspects," Comprehensive Analytical Chemistry XL, 2003, Chapter 1, pp. 1-49.

"7.2. Ethoxylates," Ullmann-Surfactants, Jan. 24, 2006, pp. 59-67.

Shinetsu Chemical Co. Ltd., "Antireflection film material and pattern forming method," Patent Abstracts of Japan, Publication Date: May 18, 2001; English Abstract of JP2001-133984.

Mita Industrial Co Ltd., "Toner Replenishment Device for image forming device and toner cartridge used therefore," Patent Abstracts of Japan, Publication Date: Nov. 13, 1998; English Abstract of JP10-301379.

International Search Report for PCT/EP2007/005840 dated Oct. 16, 2007.

"Perfluoroalkyl-substituted Alkanoic Acids," Database Caplus [online]. Retrieved from STN Database accession No. 1982:471949. abstract., Jan. 17, 2008.

Abe, T. et al., "The Electrochemical Fluorination of Nitrogen-Containing Carboxylic Acids. Fluorination of Methyl Esters of 3-diakylamino Propionic Acids," Journal of Fluorine Chemistry, 1992, vol. 57, pp. 101-111.

Agency of IND Science & Technol., "Novel perfluoroalkenylamine and production thereof," Patent Abstract of Japan, Publication Date: Mar. 15, 1989; English Abstract of JP-64 070444.

Agency of IND Science & Techonology, "Novel nitrogen-containing perfluoropropenes and production thereof," Patent Abstract of Japan, Publication Date: Mar. 15, 1989; English Abstract of JP-64 070443.

Alexander, E. S. et al., "Polyfluoroalkyl Compounds of Silicon. Part IX. Silanes containing the Bis(trifluoromethyl)amino-group," Journal of the Chemical Society, Section A: Inorganic, Physical and Theoretical Chemistry, 1970, pp. 2285-2291.

Alexander, E. S. et al., "Polyfluoroalkyl Derivatives of Nitrogen. XXXVII. Reactions of N, N-bis (trifluoromethyl)Vinylamine," Journal of the Chemical Society [Section] C: Organic 1968, vol. 7, pp. 796-801.

Banks, R. E. et al., "Nitroxide Chemistry. Part IV. Reaction of Bistrifluoromethyl Nitroxide with Aldehydes," Journal of Chemical Society, 1973, pp. 80-82.

Beilstein Ref: 4-03-00-00276 (Reg. # 1737836), 1959.
Beilstein Ref: 4-03-00-00276 (Reg. # 1745846), 1959.
Beilstein Ref: 4-03-00-00276 (Reg. # 1754890), 1957.
Beilstein Ref: 5-04 (Reg. # 1908404), 1969.
Beilstein Ref: 5-04 (Reg. # 2364247), 1964.
Beilstein Ref: 5-04,6-04 (Reg. #2043866), 1971.
Beilstein Ref: 6-03 (Reg. # 6380369), 1988.
Beilstein Ref: 6-04 (Reg. # 4994102), 1980.

Central Glass Co Ltd., "Method for producing optically active alpha-methyl-bis-3,5-(Tri-fluotomethyl) Benzylamine," Patent Abstracts of Japan, Publication Date: Oct. 23, 2001; English Abstract of JP-2001 294568.

Coy, D. H. et al., "Polyfluoroalkyl Derivatives of Nitrogen. Part XXXVIII. Reaction of N-Bromobistrifluoromethylamine with Allyl Chloride; Preparation of NN-Bistrifluoromethylprop-2-enylamine," Journal of the Chemical Society, Perkin Translations 1, Chemical Society, 1971, pp. 1062-1065.

Crimmins, M. et al., "Asymmetric Total Synthesis of (+)-Milbemycin D," Journal of the American Chemical Society, vol. 118, 1996, pp. 7513-7528.

Database WPI Week 200534. Derwent Publications Ltd. 24, Mar. 2005.

English, R. et al., "Characterization of Photooxidized Self-assembled Monolayers and Bilayers by Spontaneous Desorption Mass Spectrometry", Analytical Chemistry, 2000, vol. 72, No. 24, pp. 5973-5980.

Falbe, J., Surfactants in Consumer Products: Theory, Technology, and Application, 1987, Springer Verlag, 10 pages.

Fawcett, F. S. et al., "Organic and Biological Chemistry," Journal of the American Chemical Society, 1962, vol. 22, pp. 4275-4285.

Fernandes, T. R. et al., "Organosilicon Chemistry. Part 21. Reactions of NN-bistrifluoromethylamino-oxyl and Perfluoro (2,4-dimethyl-3-oxa-2, 4-diazapentane) with Vinylsilanes, and Pyrolysis of the Resulting Adducts," Journal of the Chemical Society, Dalton Transactions: Inorganic Chemistry, 1978, vol. 9, pp. 1024-1031.

Fleming, G. L. et al., "Polyfluotoalkyl Derivatives of Nitrogen. XXX Reaction of N-chlorobis (trifluoromethyl)Amine with Propene and Vinyl Fluoride and of N-iodobis(trifluoromethyl)Amine with Vinyl Fluoride Under Ionic Conditions," Journal of the Chemical Society [Section] C: Organic 1971, vol. 22, pp. 3829-3833.

Freear, J. et al., "Fluorinated acetylenes. I. Preparation of N, N-bisfluoromethylethynylamines," Journal of the Chemical Socieity [Section] C: Organic 1968: 1096-1103, XP-002465066.

Haas, A. et al., "Catalytic addition of trihalogenomethanesulfenyl Chlorides to olefinic compounds," Journal of Fluroine Chemistry, 1985, pp. 203-210.

Harris, J. F., "Free-radical reactions of fluoroalkanesulfenyl halides. II. Free-radical reactions of trifluoromethanesulfenyl chloride with alkanes," Journal of Organic Chemistry, Database CAPLUS on STN, 1966, vol. 31. No. 3, pp. 931-935.

Haszeldine, Robert N. et al., "Polyfluoroalkyl Derivatives of Nitrogen. Part 44. The Reactions of N-bromobis (trifluoromethyl)Amine with Open-chain, 1, 3-dienes and Cyclohexene under Ionic Conditions," Journal of the Chemical Society, 1980, vol. 2, pp. 372-377.

Hayashi, E. et al., "Decompositions and Removal of Fluorine-containing Carboxylic Acid or its Salt, Used e.g. as Surfactants, Involves Adjusting Temperature or Alkali Conditions of Acid or Salt, Decomposing and Removing Fluorine." Derwent Publications, Ltd., Publication Date: Sep. 25, 2003: English Abstract of JP 2003 267900.

Hayashi, E. et al., "Method for decomposing and removing fluorine-containing carboxylic acid or its salts," National Institute of Advanced Industrial Science and Technology, Japan, Sep. 25, 2003, XP-002465054.

Hayashi, E. et al., "New Fluorine-containing Oligomer—With Repeating Units of Formula (1) and (2)," Agency of Ind Sci & Technology, Publication Date: Mar. 7, 2007; English Abstract of JP-2000 072735.

Hayashi, E. et al., "Study on the Preparation and Solution Property of Fluroine-Containing Oligomeric Surfactants by the Use of Nitrogen-containing Perfluorocarboxylic Acids," Journal of the Japan Society of Colour Material, 1999, pp. 765-770, XP-009094640.

International Search Report of PCT/EP2007/005838 dated Aug. 22, 2007.

Knunyants, L. et al., "An unusual reaction of alpha-cyano-alpha-hydroperfluoroalkyl phosphate with Amines," Mendeleev Chemical Journal, 1977, pp. 15-105.

Konica Minolta Medical & Graphic Inc., "Silver Halide Color Photosensitive Material," Patent Abstracts of Japan, Publication Date: Mar. 24, 2005; English Abstract of JP-2005 077961.

Kraus, G. A. et al., "Model Studies for the Synthesis of Quassinoids. 1. Construction of the BCE Ring System," Journal of Organic Chemistry, 1980, vol. 45, pp. 1175-1176.

Kuhle, E. et al., "Fluorietre Isocyanate und deren Derivate als Zwischenprodukte fur biologisch active Wirkstoffe," Agnew Chem, 1977, vol. 89, pp. 797-804.

Mancuso, A. J. et al., "Oxidation of Long-chain and related alcohols of carbonyls by dimethyl sulfoxide activated by oxalyl chloride," Journal of Organic Chemistry, 1978, vol. 43, No. 12, pp. 2480-2482.

Motornyi, S. P. et al., "New esters of N-trifluoromethylcarbamic Acids," Zh. Obshch. Khim., 1959, vol. 29, pp. 2122-2124.

Munavalli, S. et al., "Unusual reactions of trifluoromethylsulfenyl chloride and trifluoromethylthiocopper with five membered heterocyclic compounds," Database CAPLUS on STN,1998, pp. 167-176.

Munavalli, S. et al., "Trifluoromethylthiocopper catalyzed oxirane ring opening," Phosphorus, Sulfer and Silicon and the Related Elements, 2004, vol. 179, No. 8, pp. 1657-1671.

Nelson, D. J. et al., "Simplified Method of Ascertaining Steric Effects in Electrophilic Addition Reactions. A Comparison of Bromination; Oxymercuration and Hydroboration," Journal of the American Chemcial Society, 1989, pp. 1414-1418.

Petrov, K. A. et al., "Synthesis of Secondary Amines with a Trifluoromethyl Group," Zh. Obshsch. Khim, 1959, vol. 29, pp. 2135-2139.

Riess, J. G. et al., "Carbohydrate- and Related Polyol-Derived Fluorosurfactants : An Update", Carbohydrate Research, vol. 327 (2000) pp. 147-168.

Sagami Chem Res Center, "Perfluoroalkyl substituted alkylcarbosylic acid," Patent Abstract of Japan, Publication Date: Dec. 26, 1981; English Abstract of JP-56 169666.

Sagami Chem Res Center, "Perfluoroalkylthio Compound," Patent Abstracts of Japan, Publication Date: Jul. 5, 1982; English Abstract of JP-57 108064.

Szonyi, F. et al., "Monodisperse non-ionic fluoroalkyl surfactants," Journal of Fluorine Chemistry, 1987, vol. 36, No. 2, pp. 195-209.

XP-002458072—Database Accession No. 2000-805382, 2007.

XP-002458073—Database Accession No. 1988: 509861, 2007.

XP-002458074—Database Accession No. 2785147, 2786929, 1974.

XP-002458075—Database Accession No. 7735809, 7738271, 1996.

XP-002458076—Database Accession No. 5843062, 5841578, 5839854, 5835796, 1992.

XP-002458077—Database Accession No. 1678484, 1678483, 1977.

XP-002458078—Database Accession No. 1985:187077, 2007.

Yoshizaki, H. et al., The first total synthesis of Re lipopolysaccharide, 2000, Nippon Kagakkai, abstract (20 pages).

Dainippon Pharmaceutical Co. Ltd., "Sulfonic acid derivative and salt thereof," Patent Abstracts of Japan, Publication Date: Nov. 24, 1987; English Abstract of JP-62 270555.

* cited by examiner

FLUOROSURFACTANTS

The present invention relates to fatty acid alkanolamides or polyolamides containing at least one group Y, where Y stands for $CF_3-(CH_2)_a-O-$, $SF_5-$, $CF_3-(CH_2)_a-S-$, $CF_3CF_2S-$, $[CF_3-(CH_2)_a]_2N-$ or $[CF_3-(CH_2)_a]NH-$, where a stands for an integer selected from the range from 0 to 5, or

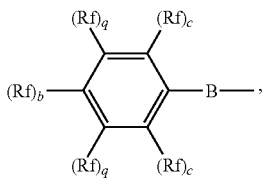

where

Rf stands for $CF_3-(CH_2)_r-$, $CF_3-(CH_2)_r-O-$, $CF_3-(CH_2)_r-S-$, $CF_3CF_2-S-$, $SF_5-(CH_2)_r-$ or $[CF_3-(CH_2)_r]_2N-$, $[CF_3-(CH_2)_r]NH-$ or $(CF_3)_2N-(CH_2)_r-$, B stands for a single bond, O, NH, NR, $CH_2$, $C(O)-O$, $C(O)$, S, $CH_2-O$, $O-C(O)$, $N-C(O)$, $C(O)-N$, $O-C(O)-N$, $N-C(O)-N$, $O-SO_2$ or $SO_2-O$, R stands for alkyl having 1 to 4 C atoms, b stands for 0 or 1 and c stands for 0 or 1, q stands for 0 or 1, where at least one radical from b and q stands for 1, and r stands for 0, 1, 2, 3, 4 or 5, to processes for the preparation of these compounds, and to uses of these surface-active compounds.

Fluorosurfactants have an outstanding ability to reduce surface energy, which is utilised, for example, in the hydrophobicisation of surfaces, such as textile impregnation, hydrophobicisation of glass, or de-icing of aircraft wings.

In general, however, fluorosurfactants contain perfluoroalkyl substituents, which are degraded in the environment by biological and other oxidation processes to give perfluoroalkanecarboxylic acids and -sulfonic acids. These are regarded as persistent and are in some cases suspected of causing health damage (G. L. Kennedy, Jr., J. L. Butenhoff, G. W. Olsen, J. C. O'Connor, A. M. Seacat, R. G. Perkins, L. B. Biegel, S. R. Murphy, D. G. Farrar, Critical Reviews in Toxicology 2004, 34, 351-384). In addition, relatively long-chain perfluoroalkanecarboxylic acids and -sulfonic acids accumulate in the food chain.

There is therefore a demand for surface-active substances which have a property profile comparable to the classical fluorosurfactants and which can preferably be degraded oxidatively or reductively. Particularly advantageous compounds here are those which do not leave behind any persistent organofluorine degradation products on degradation.

The Omnova company markets polymers whose side chains contain terminal $CF_3$ or $C_2F_5$ groups. International patent application WO 03/010128 describes perfluoroalkyl-substituted amines, acids, amino acids and thioether acids which contain a $C_{3-20}$-perfluoroalkyl group.

JP-A-2001/133984 discloses surface-active compounds containing perfluoroalkoxy chains which are suitable for use in antireflection coatings. JP-A-09/111286 discloses the use of perfluoropolyether surfactants in emulsions.

However, these known fluorosurfactants ultimately result in the formation of persistent perfluoroalkanesulfonic acids and -carboxylic acids on degradation. Even the substitutes containing a terminal $CF_3$ group which have been introduced as being more ecologically friendly can be degraded to give persistent trifluoroacetic acid.

The earlier German patent application DE 102005000858 describes compounds which carry at least one terminal pentafluorosulfuranyl group or at least one terminal trifluoromethoxy group and contain a polar end group, are surface-active and are highly suitable as surfactants.

Fatty acid alkanolamides or polyolamides which contain no F atoms are known as surfactants. These nonionic alkanolamides or polyolamides, called fatty acid glucamides in the case of glucosamine, are used, for example, in detergents according to British Patent 809 060, published in 1959, or according to Hildreth et al., Biochem. J. 1982, Vol. 207, pages 363-366, or for cleaning hard surfaces, according to U.S. Pat. No. 2,708,798. Alkanolamides are foam boosters which enhance or stabilise the foam. Ethoxylated alkanolamides are used as thickeners, foam stabilisers or dispersants.

This class of fatty acid alkanolamides or polyolamides containing $OCF_3$ or $SF_5$ groups as modification was not described in DE 102005000858.

There continues to be a demand for further, preferably degradable substitutes for perfluorinated surfactants.

It has now been found that the fatty acid alkanolamides or polyolamides according to the invention containing at least one group Y, where Y stands for $CF_3-(CH_2)_a-O-$, $SF_5-$, $CF_3-(CH_2)_a-S-$, $CF_3CF_2S-$, $[CF_3-(CH_2)_a]_2N-$ or $[CF_3-(CH_2)_a]NH-$, where a stands for an integer selected from the range from 0 to 5, or

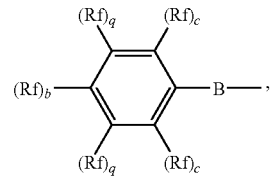

where

Rf stands for $CF_3-(CH_2)_r-$, $CF_3-(CH_2)_r-O-$, $CF_3-(CH_2)_r-S-$, $CF_3CF_2-S-$, $SF_5-(CH_2)_r-$ or $[CF_3-(CH_2)_r]_2N-$, $[CF_3-(CH_2)_r]NH-$ or $(CF_3)_2N-(CH_2)_4-$, B stands for a single bond, O, NH, NR, $CH_2$, $C(O)-O$, $C(O)$, S, $CH_2-O$, $O-C(O)$, $N-C(O)$, $C(O)-N$, $O-C(O)-N$, $N-C(O)-N$, $O-SO_2$ or $SO_2-O$, R stands for alkyl having 1 to 4 C atoms, b stands for 0 or 1 and c stands for 0 or 1, q stands for 0 or 1, where at least one radical from b and q stands for 1, and r stands for 0, 1, 2, 3, 4 or 5, are surface-active and are highly suitable as surfactants.

The invention therefore relates firstly to fatty acid alkanolamides or polyolamides containing at least one group Y, where Y stands for $CF_3-(CH_2)_a-O-$, $SF_5-$, $CF_3-(CH_2)_a-S-$, $CF_3CF_2S-$, $[CF_3-(CH_2)_a]_2N-$ or $[CF_3-(CH_2)_a]NH-$, where a stands for an integer selected from the range from 0 to 5, or

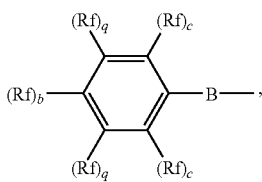

where

Rf stands for $CF_3-(CH_2)_r-$, $CF_3-(CH_2)_r-O-$, $CF_3-(CH_2)_r-S-$, $CF_3CF_2-S-$, $SF_5-(CH_2)_r-$ or $[CF_3-(CH_2)_r]_2N-$, $[CF_3-(CH_2)_r]NH-$ or $(CF_3)_2N-(CH_2)_r-$, B stands for a single bond, O, NH, NR, $CH_2$, $C(O)-O$, $C(O)$, S, $CH_2-O$, $O-C(O)$, $N-C(O)$, $C(O)-N$, $O-C(O)-N$, $N-C(O)-N$, $O-SO_2$ or $SO_2-O$, R stands for alkyl having 1 to 4 C atoms, b stands for 0 or 1 and c stands for 0 or 1, q stands for 0 or 1, where at least one radical from b and q stands for 1, and r stands for 0, 1, 2, 3, 4 or 5.

The compounds according to the invention preferably contain no further fluorinated groups besides the fluorinated groups Y mentioned.

The fatty acid amides according to the invention are derived from fatty acids, which may be saturated or unsaturated and contain 4 to 25 C atoms, preferably 8 to 22 C atoms, particularly preferably 12 to 20 C atoms. The fatty acids may also carry, for example, OH groups in the side chain.

Examples of fatty acids are lauric acid ($C_{11}H_{23}COOH$), myristic acid ($C_{13}H_{27}COOH$), palmitic acid ($C_{15}H_{31}COOH$), stearic acid ($C_{17}H_{35}COOH$), oleic acid ($C_{17}H_{33}COOH$), linoleic acid ($C_{17}H_{31}COOH$), ricinoleic acid ($C_{17}H_{32}(OH)COOH$), linolenic acid ($CH_3CH_2CH=CHCH_2CH=CH_2CH=CH(CH_2)_7COOH$), arachidonic acid ($C_{19}H_{39}COOH$) or erucic acid ($C_{21}H_{43}COOH$).

In a variant of the invention, preference is given to fatty acids having an even number of carbons, i.e. preferably having 8, 10, 12, 14, 16, 18, 20 or 22 C atoms, particularly preferably having 12, 14, 16, 18 or 20 C atoms. However, it is also possible to employ synthetic fatty acids having an odd number of carbons.

In the fatty acid amides according to the invention, the group Y is preferably in the terminal position to the amide function. In fatty acids containing free OH groups in the side chain, these may likewise be replaced by Y, in particular by the group Y selected from the moiety $CF_3-O-$, $CF_3-(CH_2)_a-O-$, where a=1, 2, 3, 4 or 5, or

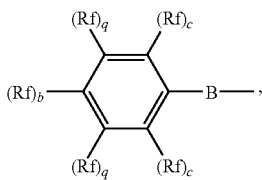

where

Rf stands for $CF_3-(CH_2)_r-$, $CF_3-(CH_2)_r-O-$, $CF_3-(CH_2)_r-S-$, $CF_3CF_2-S-$, $SF_5-(CH_2)_r-$ or $[CF_3-(CH_2)_r]_2N-$, $[CF_3-(CH_2)_r]NH-$ or $(CF_3)_2N-(CH_2)_r-$, B stands for a single bond, O, NH, NR, $CH_2$, $C(O)-O$, $C(O)$, S, $CH_2-O$, $O-C(O)$, $N-C(O)$, $C(O)-N$, $O-C(O)-N$, $N-C(O)-N$, $O-SO_2$ or $SO_2-O$, R stands for alkyl having 1 to 4 C atoms, b stands for 0 or 1 and c stands for 0 or 1, q stands for 0 or 1, where at least one radical from b and q stands for 1, and r stands for 0, 1, 2, 3, 4 or 5.

The compounds according to the invention are preferably compounds of the formula I

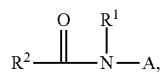

where $R^1$ denotes H, alkyl having 1 to 4 C atoms or hydroxyalkyl having 2 to 4 C atoms, $R^2$ denotes a fatty acid radical containing at least one group Y as defined above, and A denotes $-CH_2-(CHOH)_n-CH_2-OH$, where n=3, 4 or 5, $-(CH_2)_m-OH$, where m=1 to 20, $-(CH_2CH_2O)_p-H$, where p=1 to 9, $-(CH_2CH_2CH_2O)_p-H$, where p=1 to 9, or $-(CH_2CH_2CH_2CH_2O)_p-H$, where p=1 to 9, where the ethyleneoxy, propyleneoxy and butyleneoxy units may also occur in mixed form in the chain.

In the formula I, $N-R^1$ may, for example, be NH, N-methyl, N-ethyl, N-propyl, N-isopropyl, N-butyl, N-isobutyl, N-2-hydroxyethyl or N-2-hydroxypropyl.

In a variant of the invention, preference is given to compounds in which A denotes $-CH_2-(CHOH)_n-CH_2-OH$, where n=3, 4 or 5. In this case, A is derived from a reducing carbohydrate in a reductive amination reaction. These fatty acid amides are also called fatty acid polyolamides, for n=4 preferably fatty acid glucamides.

Examples of reducing sugars (or also synonymously carbohydrates) are ribose, arabinose, xylose, lyxose, allose, altrose, glucose, mannose, gulose, idose, galactose, talose, ribulose, xylulose, psicose, fructose, sorbose or tagatose. This list includes both isomers, i.e. in each case the D or L forms.

From the group of these monosaccharides, preference is given to the use of glucose or galactose, very particularly glucose.

However, it is also possible to employ disaccharides, such as saccharose (or also called sucrose), lactose, trehalose, maltose, cellobiose, gentiobiose or melibiose. This list includes both the α and β forms.

From the group of the disaccharides, preference is given to the use of saccharose or lactose.

Starting materials which can be used for reducing sugars are also starch sugar syrup, for example from maize, where this syrup may comprise mixtures of reducing carbohydrates. Fatty acid polyolamides based on this starting material are accordingly mixtures which, however, can also be employed as mixtures in the uses according to the invention.

In a variant of the invention, preference is given to compounds in which A denotes $-(CH_2)_m-OH$, where m=1 to 20. In this case, A is derived from an amine $HNR^1-(CH_2)_m-OH$, where m=1 to 20. Preferred compounds are compounds where m=2, 3, 4, 5, 6, 7, 8, 9, 10, 11, 12, 13, 14, 15, 16, 17 or 18, particularly preferably where m=4, 5, 6, 7 or 8.

In a variant of the invention, preference is given to compounds in which

A is —$(CH_2CH_2O)_p$—H, —$(CH_2CH_2CH_2O)_p$—H or —$(CH_2CH_2CH_2CH_2O)_p$—H, where p=1 to 9, preferably —$(CH_2CH_2O)_p$—H or —$(CH_2CH_2CH_2O)_p$—H, where p=1 to 9, where the ethyleneoxy, propyleneoxy and butyleneoxy units may also occur in mixed form in the chain. p is preferably 2, 3, 4, 5, 6 or 7, very particularly preferably 2, 3 or 4.

In this case, A is derived from an amine $HNR^1$—$(CH_2)_m$—OH, where m=2, 3 or 4, where the chain can then be extended by reaction with ethylene oxide, propylene oxide or butylene oxide.

In the group Y, a preferably stands for 0, 1 or 2, particularly preferably for 0 or 2, very particularly preferably for 0, and r preferably stands for 0 to 3, in particular 0 to 1.

In a variant of the present invention, it is preferred for q in the group Y to stand for 0 and for at least one c and/or b each to stand for 1. It is particularly preferred for all c and b to stand for 1, i.e. the aromatic rings are substituted by fluorine groups in the o- and/or p-position, in particular in the o,p,o-position.

In a further variant of the invention, it is preferred for all q and b each to stand for 0 and for at least one c to stand for 1. It is particularly preferred for both c to stand for 1, i.e. the aromatic rings are substituted by fluorine groups in the o-position, in particular in the o,o-position.

In a further variant of the invention, it is preferred for all c and q each to stand for 0 and for b to stand for 1, i.e. the aromatic rings are substituted by fluorine groups in the p-position.

Of the fluorine groups as aryl substituents, preference is given to those in which r stands for 0, 1 or 2, where r preferably stands for 0. Particular preference is given in accordance with the invention to the groups Rf=$CF_3$—, $CF_3$—S—, $CF_3CF_2$—S—, $SF_5$— or $(CF_3)_2N$—.

In a preferred variant of the invention, the group Y, as defined above, which determines the modification of the fatty acid consists of $CF_3$—O—, $CF_3$—$CF_2$—S—, $CF_3$—S—, $(CF_3)_2N$— or where
Rf stands for $CF_3$—$(CH_2)_r$—, $CF_3$—$(CH_2)_r$—O—, $CF_3$—$(CH_2)_r$—S—, $CF_3CF_2$—S—, $SF_5$—$(CH_2)_r$— or [$CF_3$—$(CH_2)_r$]$_2N$—, [$CF_3$—$(CH_2)_r$]NH— or $(CF_3)_2N$—$(CH_2)_r$—, B stands for a single bond, O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O, R stands for alkyl having 1 to 4 C atoms, b stands for 0 or 1 and c stands for 0 or 1, q stands for 0 or 1, where at least one radical from b and q stands for 1, and r stands for 0.

Rf preferably stands for $CF_3$—$(CH_2)_r$—, $CF_3$—$(CH_2)_r$—O—, $CF_3$—$(CH_2)_r$—S or [$CF_3$—$(CH_2)_r$]$_2N$—. A preferred variant of the invention encompasses fluorine groups, also abbreviated to Rf below, in which r stands for 0, 1, 2 or 3, in particular for 0, 1 or 2, where r preferably stands for 0.

In a particularly preferred embodiment of the present invention, Rf stands for $CF_3$—, $CF_3$—O—, $CF_3$—$CH_2$—$CH_2$—O—, $CF_3$—S—, $CF_3CF_2$—S—, $SF_5$—, $CF_3$—$CH_2$—$CH_2$—S—, $(CF_3)_2$—N— and $(CF_3$—$CH_2$—$CH_2)_2$—N—, in particular for $CF_3$—, $CF_3$—O—, $CF_3$—S— and $(CF_3)_2$—N—.

A further preferred variant of the invention encompasses the groups Rf which are equal to $CF_3$—, $CF_3$—S—, $CF_3CF_2$—S—, $SF_5$— or $(CF_3)_2N$—.

Particularly preferred groups B are O, S, $CH_2O$, $CH_2$, C(O) and OC(O). In particular, B equal to O and OC(O) are preferred.

A particularly preferred variant of the invention encompasses the groups Y which are equal to $CF_3$—Ar—O, $CF_3$—O—Ar—O, $CF_3$—$CH_2$—$CH_2$—O—Ar—O, $CF_3$—S—Ar—O, $CF_3CF_2$—S—Ar—O, $SF_5$—Ar—O, $CF_3$—$CH_2$—$CH_2$—S—Ar—O, $(CF_3)_2$—N—Ar—O, $(CF_3$—$CH_2$—$CH_2)_2$—N—Ar—O, $CF_3$—Ar—OC(O), $CF_3$—O—Ar—OC(O), $CF_3$—$CH_2$—$CH_2$—O—Ar—OC(O), $CF_3$—S—Ar—OC(O), $CF_3CF_2$—S—Ar—OC(O), $SF_5$—Ar—OC(O), $CF_3$—$CH_2$—$CH_2$—S—Ar—OC(O), $(CF_3)_2$—N—Ar—OC(O) and $(CF_3$—$CH_2$—$CH_2)_2$—N—Ar—OC(O), in particular equal to $CF_3$—Ar—O, $CF_3$—O—Ar—O, $CF_3$—S—Ar—O, $(CF_3)_2$—N—Ar—O, $CF_3$—Ar—OC(O), $CF_3$—O—Ar—OC(O), $CF_3$—S—Ar—OC(O) and $(CF_3)_2$—N—Ar—OC(O).

A particularly preferred variant of the invention encompasses Y equal to $CF_3$—Ar—O and $CF_3$—Ar—OC(O).

In a variant of the present invention, it is preferred for q to stand for 0 and for at least one c and/or b each to stand for 1. It is particularly preferred for all c and b to stand for 1, i.e. the aromatic rings are substituted by fluorine groups in the o,p,o-position.

In a further variant of the invention, it is preferred for all q and b each to stand for 0 and for at least one c to stand for 1. It is particularly preferred for both c to stand for 1, i.e. the aromatic rings are substituted by fluorine groups in the o,o-position.

In a further variant of the invention, it is preferred for all c and q each to stand for 0 and for b to stand for 1, i.e. the aromatic rings are substituted by fluorine groups in the p-position.

Particular preference is given to the use of compounds which have a combination of the variables in their preferred or particularly preferred ranges.

Further preferred combinations are disclosed in the claims.

The particularly preferred compounds of the fatty acid alkanolamides or polyolamides include the following compounds:

$F_5S$—CH=CH—$(CH_2)_7$—C(O)—N(—/—O—/—O—)$_w$—OH w = 3 to 8

-continued
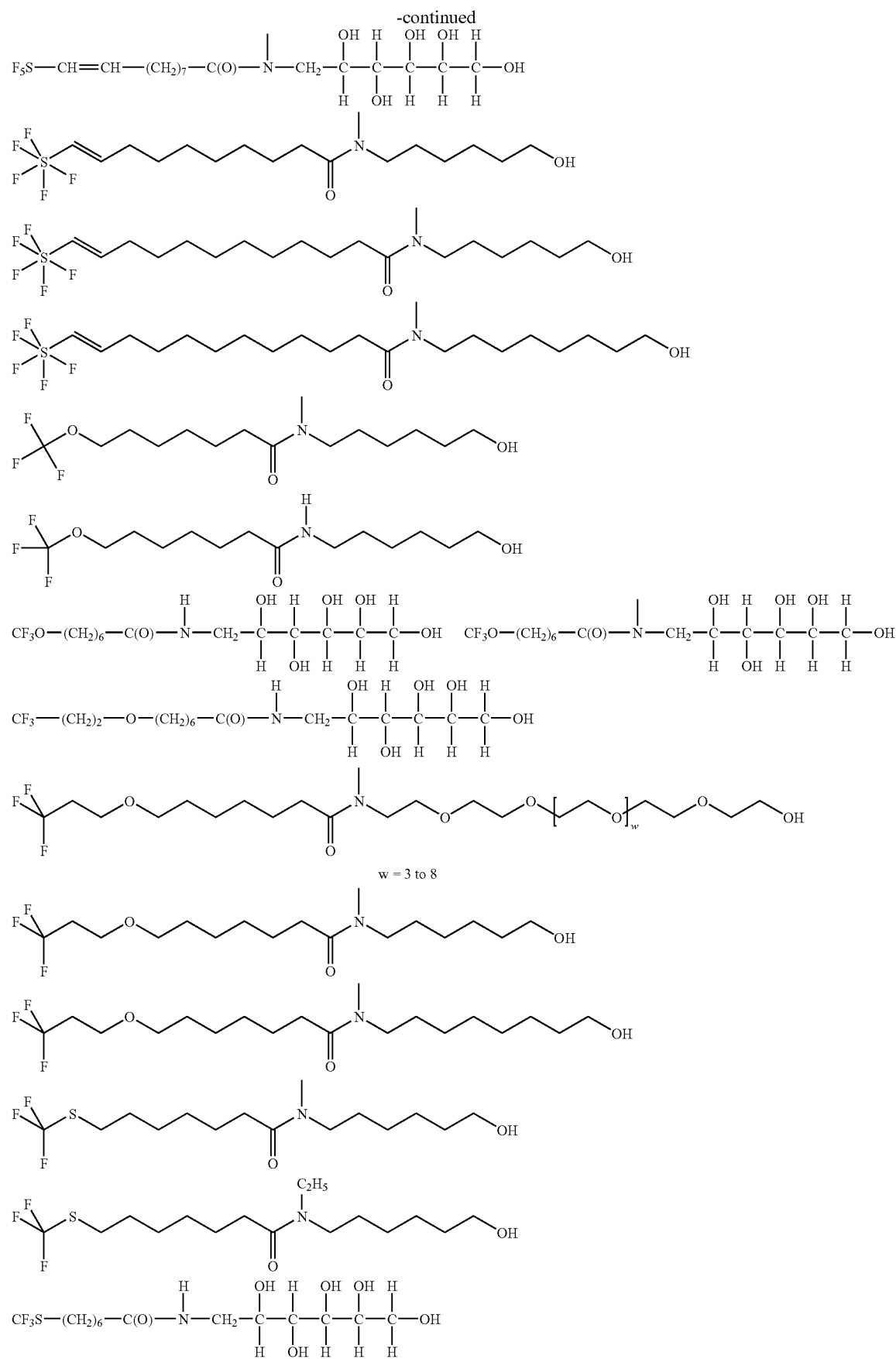

-continued

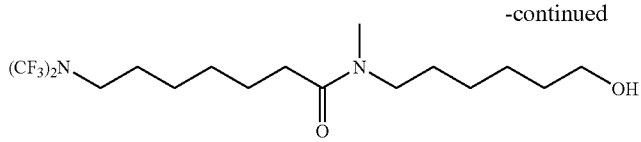

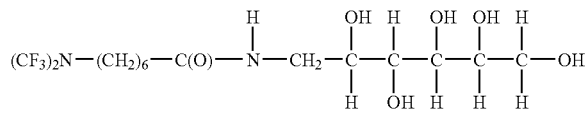

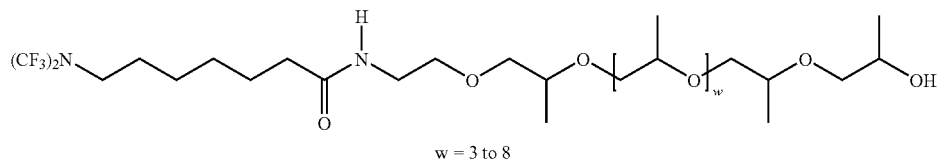

w = 3 to 8

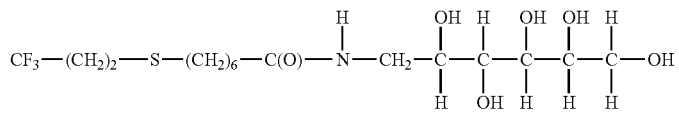

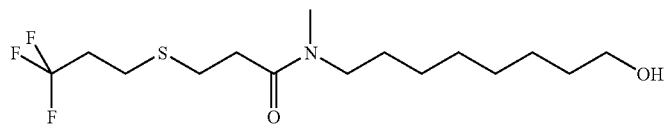

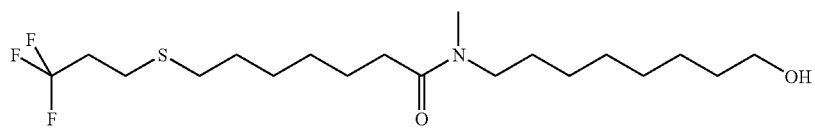

The fatty acid amides according to the invention can be prepared by methods known per se to the person skilled in the art from the literature.

The invention therefore furthermore relates to a process for the preparation of the fatty acid alkanolamides or polyolamides according to the invention, characterised in that a fatty acid containing the group Y, as defined above, or a derivative of this fatty acid, preferably an acid chloride, an active ester or an anhydride, is reacted with an alkanolamine or polyolamine.

Derivatives of the modified fatty acid whose synthesis is described in detail below are, for example, the fatty acid chlorides thereof or lower esters of these fatty acids, in particular the methyl esters, active esters or anhydrides.

Particular preference is given to the reaction of modified fatty acid esters, particularly preferably methyl esters, with the corresponding amines in an organic solvent in the presence of a base catalyst. The acid chlorides are very particularly preferably reacted with the corresponding amines in an organic solvent in the presence of a base catalyst.

Suitable basic catalysts are alkoxides, hydroxides or carbonates or amines. Preference is given to the use of alkoxides, such as sodium methoxide, potassium ethoxide. An amine which is preferably employed is triethylamine. Suitable solvents for the conversion to N-polyolamides are organic solvents, such as methanol, ethanol, propanol, isopropanol, butanols, glycerol, 1,2-propylene glycol, 1,3-propylene glycol, or also mixtures of these solvents. The reaction is preferably carried out below 100° C. However, a suitable solvent is also tetrahydrofuran.

The synthesis of the fatty acid polyolamides, in particular the glucamides, and the synthesis of the polyolamines (synonymously N-alkylpolyhydroxyamines) are described in detail in EP 0 558 515 or in U.S. Pat. No. 2,703,798. The corresponding disclosure of the said method in EP 0 558 515 or U.S. Pat. No. 2,703,798 thus expressly also belongs to the disclosure content of the present application.

The N—$R^1$-polyhydroxyamines can be prepared, for example, by reaction of a reducing carbohydrate or reducing carbohydrate derivative with a primary amine at molar ratios of amine:carbohydrate of not more than about 7:1 in a suitable solvent. The suitable reaction temperature is between 0° C. and 80° C. The adduct formed is reacted further under inert-gas conditions with hydrogen under mild conditions in the presence of a catalyst, for example Raney nickel or nickel adhering to silicon dioxide or aluminium oxide, and the catalyst and the water formed are removed.

However, N—$R^1$-polyhydroxyamines, such as, for example, N-methylglucamine, are also commercially available.

The synthesis of the fatty acid alkanolamides, i.e. the compounds in which A denotes —$(CH_2)_m$—OH, where m=1 to 20, can be carried out as described above, where the amines $HNR^1$—$(CH_2)_m$—OH, where m=1 to 20, employed are generally commercially available or can be prepared by known syntheses, as can be derived, for example, from Organikum: Organisch-Chemisches Grundpraktikum [Basic Practical Organic Chemistry], 16th Edn., VEB Deutscher Verlag der Wissenschaften, Berlin, 1986.

The synthesis of the ethoxylated, propoxylated or butoxylated fatty acid alkanolamides, i.e. the compounds in which A denotes —$(CH_2CH_2O)_p$—H, —$(CH_2CH_2CH_2O)_p$—H or —$(CH_2CH_2CH_2CH_2O)_p$—H, where p=1 to 9, preferably —$(CH_2CH_2O)_p$—H or —$(CH_2CH_2CH_2O)_p$—H, where p=1 to 9, can be carried out as described above, where firstly the fatty acid or the fatty acid derivatives are reacted with amines of the formula $HNR^1$—$(CH_2)_m$—OH, where m=2, 3 or 4, which are generally commercially available or can be prepared by known syntheses, as can be derived, for example, from Organikum: Organisch-Chemisches Grundpraktikum [Basic Practical Organic Chemistry], 16th Edn., VEB Deutscher Verlag der Wissenschaften, Berlin, 1986, and the subsequent chain extension is carried out by the known reaction with ethylene oxide, propylene oxide or butylene oxide. The addition reaction is generally carried out with base or Lewis acid catalysis. Suitable bases have already been described above. Suitable Lewis acids are, for example, boron trifluoride, tin tetrachloride or antimony pentachloride, as described, for example, in Ullmann's Encyclopedia of Industrial Chemistry 2002, Chapter 7.2, pages 59 to 114.

Examples of the synthesis of the modified saturated fatty acids are revealed by the following scheme. The synthesis of the modified unsaturated fatty acids is correspondingly analogous.

1. For the group Y=$OCF_3$ and for saturated fatty acids $CH_3$—$(CH_2)_{s-1}$—COOH, whose alkylene units are represented by $(CH_2)_s$ in the schemes, where s can be equal to 4 to 25:

Variant A:

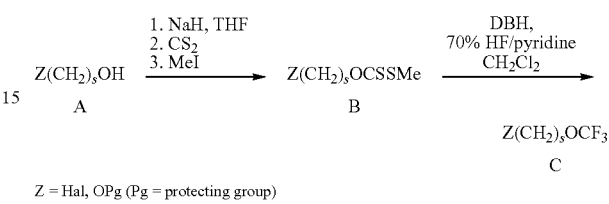

Z = Hal, OPg (Pg = protecting group)

The aliphatic $OCF_3$ group can be obtained, for example, from a precursor A=Z$(CH_2)_s$—OH via the fluorodesulfuration of xanthogenates (K. Kanie, Y. Tanaka, K. Suzuki, M. Kuroboshi, T. Hiyama, Bull. Chem. Soc. Jpn. 2000, 73, 471-484; P. Kirsch, Modern Fluoroorganic Chemistry: Synthesis, Reactivity, Applications, Wiley-VCH, Weinheim, 2004, pp. 67 ff., pp. 144 ff.). The corresponding disclosure of the said method in the cited references thus expressly also belongs to the disclosure content of the present application.

The derivatisation of the deprotected alcohol to give the acid is subsequently carried out by oxidation.

Derivatisation for Z=OPg (e.g. OBn=O-benzyl):

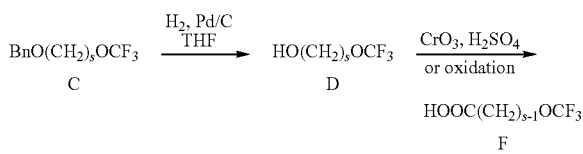

Alternatively, the modified fatty acid can be prepared by variant B:

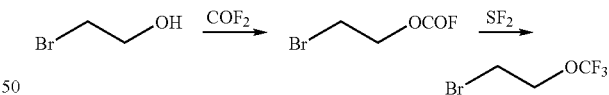

2-Bromoethanol is converted into the fluoroformate, and the carbonyl group is subsequently transformed into the $OCF_3$ ether using $SF_4$.

Literature:

1. Aldrich, P. E.; Sheppard, William A. J. Org. Chem. 1964, 29, 11-15

2. Sheppard, William A. et al. J. Org: Chem. 1964, 29, 1-11

3. Yagupol'skii, L. M.; Alekseenko, A. N.; Il'chenko, A. Y Ukrainskii Khimicheskii Zhurnal 1978, 44, 1057-1059

The fatty acid is now obtained by: 1. Williamson ether synthesis, 2. subsequent hydrogenolytic debenzylation, and 3. subsequent oxidation using stoichiometric amounts of sodium periodate and catalytic amounts of ruthenium chloride.

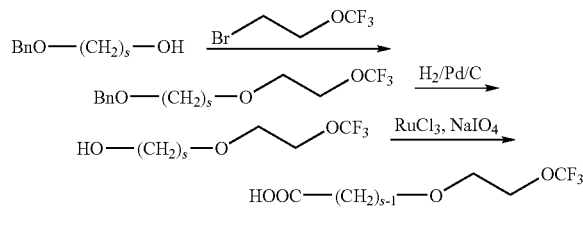

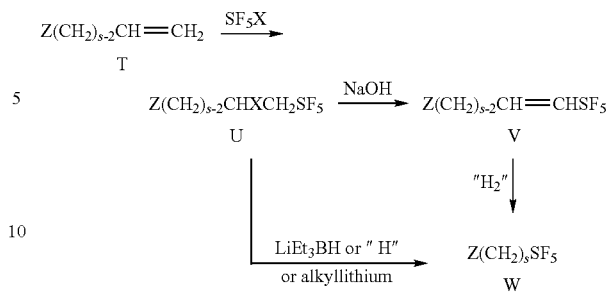

2. For the group Y=CF$_3$—(CH$_2$)$_a$—O—, where a=1 to 5, and for saturated fatty acids, whose alkylene units are represented by (CH$_2$)$_s$ in the schemes, where s can be equal to 4 to 25:

The CF$_3$—(CH$_2$)$_a$—O— group is introduced by reaction of CF$_3$—(CH$_2$)$_a$—OH, where a=1, 2, 3, 4 or 5, with a primary hydroxy ester via a Mitsunobu reaction (Mitsunobu, O. Synthesis, 1981, 1) to give the corresponding fatty acid esters.

Z = Hal, OPg(Pg = protecting group)
X = Cl, Br, I
s = 1-20

Derivatisation for Z=OPg (e.g. OBn):

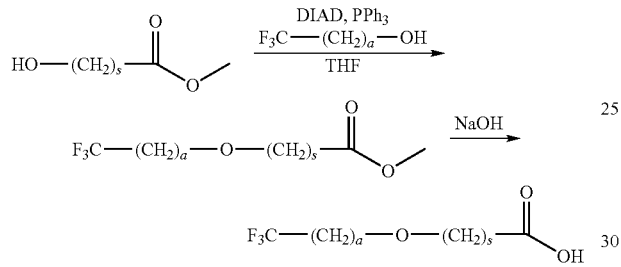

DIAD = diisopropyl azodicarboxylate

Alternatively, the modified fatty acid can also be prepared by dietherification of the alcohol CF$_3$—(CH$_2$)$_a$—OH, where a=1 to 5, onto a corresponding brominated alkene and subsequent ozonolysis with oxidative work-up.

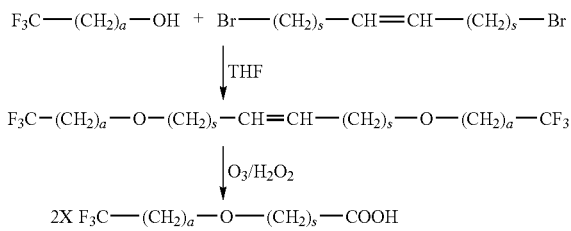

3. For the group Y=SF$_5$ and for saturated fatty acids, whose alkylene units are represented by (CH$_2$)$_s$ in the schemes, where s can be equal to 4 to 25:

The aliphatic SF$_5$ group can be introduced, for example, at terminal double bonds via the free-radical addition reaction of SF$_5$Cl or SF$_5$Br. A dehydrohalogenation or a hydrogenation, for example, can subsequently optionally be carried out. The first two of these reaction steps are described in the literature (R. Winter, P. G. Nixon, G. L. Gard, D. H. Radford, N. R. Holcomb, D. W. Grainger, J. Fluorine Chem. 2001, 107, 23-30), as are catalytic hydrogenations in the presence of an SF$_5$ function (P. Kirsch, M. Bremer, M. Heckmeier, K. Tarumi, Angew. Chem. 1999, 111, 2174-2178; Angew. Chem. Int. Ed. Engl. 1999, 38, 1989-1992). The corresponding disclosure of the said method in the cited references thus expressly also belongs to the disclosure content of the present application. Examples are revealed by the following scheme:

An alternative synthesis of the SF$_5$-modified fatty acid is the addition of SF$_5$Cl onto a terminal double bond of a fatty acid ester, for example a methyl ester, elimination of HCl and subsequent ester cleavage.

4. For the group Y=CF$_3$—S or CF$_3$—CF$_2$—S and for saturated fatty acids, whose alkylene units are represented by (CH$_2$)$_s$ in the schemes, where s can be equal to 4 to 25:

Acids or acid derivatives containing a terminal thiol group are commercially available or can be prepared by methods known to the person skilled in the art, for example as described in . . . . Conversion into the desired CF$_3$—S or CF$_3$—CF$_2$—S group is carried out, for example, in accordance with the following scheme and in accordance with Anselmi, E. et al. J. Fluorine Chem. 2000, 105, 1, 41-44 or can optionally be carried out by means of Se (trifluoromethyl) dibenzoselenophenium triflate (Umemoto's reagent): T. Umemoto et al. J. Am. Chem. Soc. 1993, 115, 2156-2164, or via: N. V. Ignatiev, Ukr. Khim. Zh. 2001, No. 10, pp. 98-102.

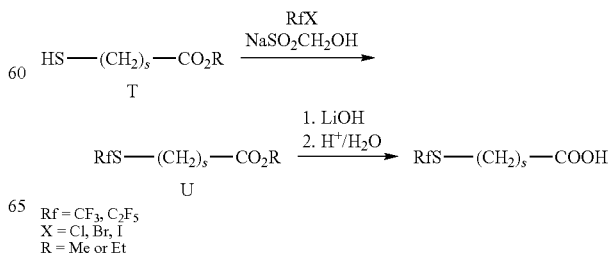

Rf = CF$_3$, C$_2$F$_5$
X = Cl, Br, I
R = Me or Et

5. For the group Y=(CF$_3$)$_2$N— and for saturated fatty acids, whose alkylene units are represented by (CH$_2$)$_s$ in the schemes, where s can be equal to 4 to 25:

The aliphatic (CF$_3$)$_2$N— group is introduced into the fatty acids firstly by reaction of corresponding tetramethylammonium salts with halides which have a corresponding number of C atoms for the desired fatty acid and a terminal double bond, in accordance with the scheme shown. The respective tetramethylammonium salts can be obtained analogously to the description of EP 1081129. The corresponding disclosure of the said method in the cited references thus expressly also belongs to the disclosure content of the present application.

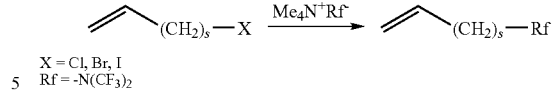

The terminal double bond can be converted into the carboxyl function by methods known to the person skilled in the art. Examples are revealed by the following scheme, where Rf in the following scheme can be N(CF$_3$)$_2$, but also SCF$_3$ or SC$_2$F$_5$:

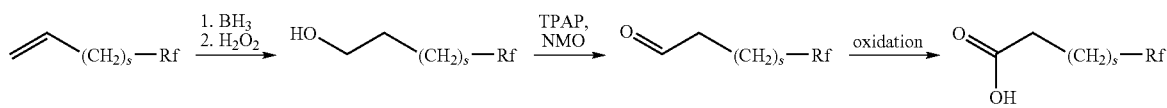

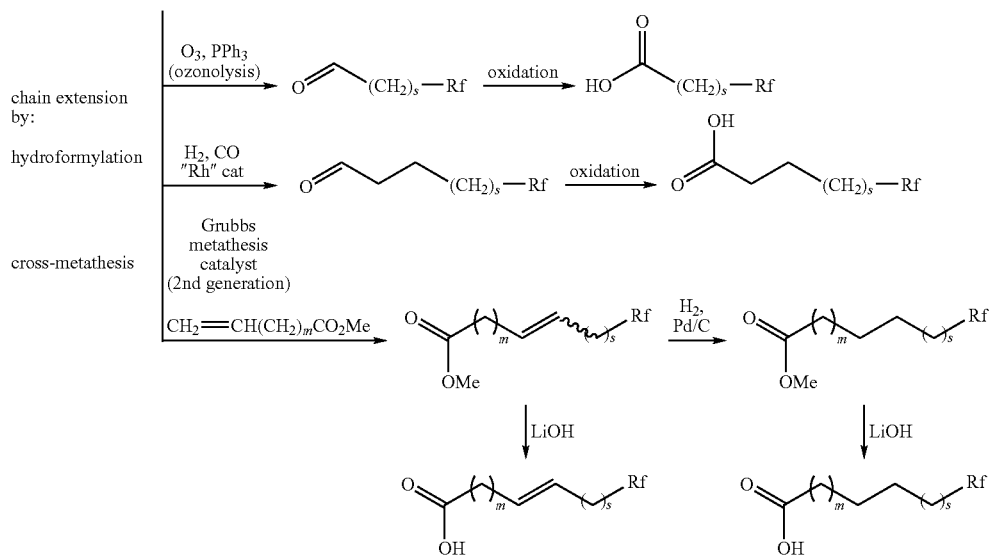

m = 1 to 20

Chain extension by Wittig reaction:

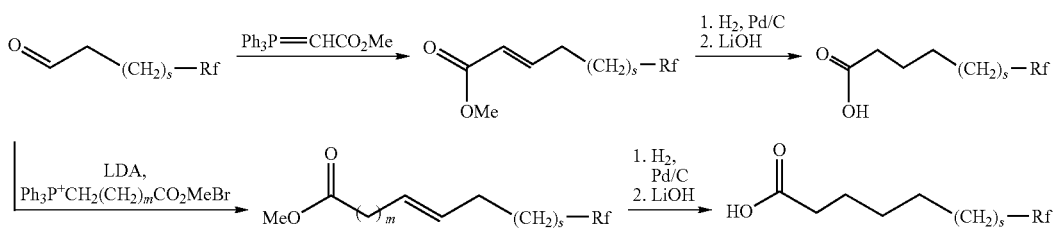

x = -1, 0, 1

The amine building block [CF$_3$—(CH$_2$)$_a$]$_2$N—, where a stands for an integer selected from the range from 1 to 5, can be introduced with the aid of the Gabriel synthesis (Organikum: Organisch-Chemisches Grundpraktikum [Basic Practical Organic Chemistry], 16th Edn., VEB Deutscher Verlag der Wissenschaften, Berlin, 1986), followed by liberation of the primary amine by reaction with hydrazine. Subsequent alkylation of this amine using CF$_3$(CH$_2$)Hal and debenzylation gives the tertiary amino alcohol as key building block.

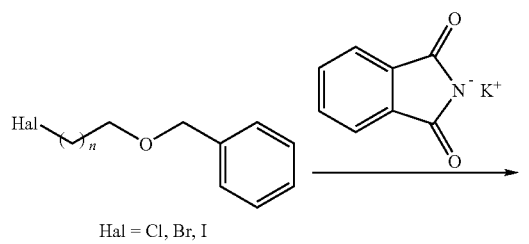

Hal = Cl, Br, I

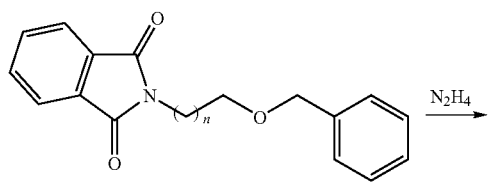

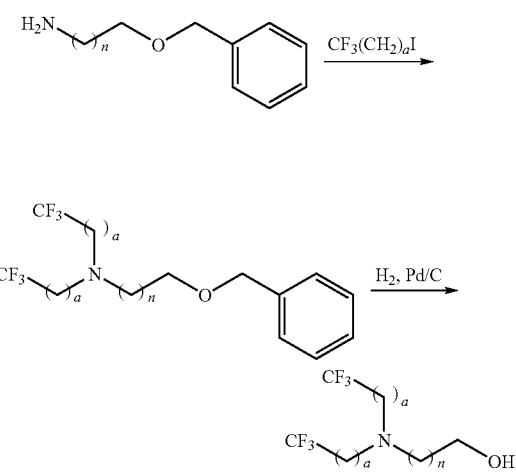

Subsequent oxidation by, for example, CrO$_3$/H$_2$SO$_4$ results in the modified acid.

6. For the group Y=CF$_3$—(CH$_2$)$_a$—S—, where a=1 to 5, and for saturated fatty acids, whose alkylene units are represented by (CH$_2$)$_s$ in the schemes, where s can be equal to 4 to 25:

The CF$_3$—(CH$_2$)$_a$—S— group is introduced, for example, by reaction of CF$_3$—(CH$_2$)$_a$—OH, where a=1, 2, 3, 4 or 5, with a fatty acid ester containing a terminal thiol group via a Mitsunobu reaction (Mitsunobu, O. Synthesis, 1981, 1) to give the corresponding fatty acid esters, where the alcohols of the formula CF$_3$—(CH$_2$)$_a$—OH are commercially available or are readily accessible from commercial substances.

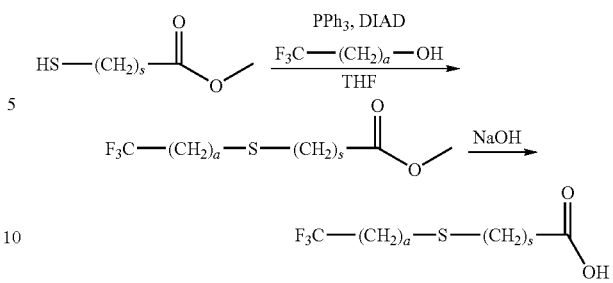

Analogously to Examples 9a-c, CF$_3$S— or CF$_3$CF$_2$S— or CF$_3$(CH)$_a$— end groups can also be introduced instead of (CF$_3$)$_2$N— end groups. In the case of sulfur-containing compounds, Pt or Ru catalysts are employed instead of Pd catalysts.

7. The following applies for the group Y=CF$_3$NH—:

The end group CF$_3$NH— in compounds CF$_3$NH—R can be introduced by methods known from the literature by reaction of corresponding compounds Cl$_2$C=N—R with an excess of HF (corresponding syntheses are described, for example, in Petrow et al., Zh. Obshch. Khim. 29 (1959) 2169-2172). Alternatively, it is also possible to react trifluoromethyl isocyanate with an alcohol to give a compound CF$_3$—NHC(=O)—O—R (as described by Knunyants et al. Mendeleev chem. J. 22 (1977) 15-105 or Motornyi et al., Zh. Obshch. Khim. 29 (1959) 2157-2122). The corresponding starting materials are each obtainable by methods known from the literature, and the radicals R of the products can be chemically modified by established methods.

8. The following applies for the group Y=

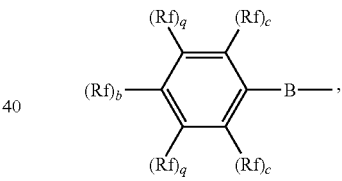

where
Rf=CF$_3$—(CH$_2$)$_r$—, CF$_3$—(CH$_2$)$_r$—O—, CF$_3$—(CH$_2$)$_r$—S—, CF$_3$CF$_2$—S—, SF$_5$—(CH$_2$)$_r$— or [CF$_3$—(CH$_2$)$_r$]$_2$N—, [CF$_3$—(CH$_2$)$_r$]NH— or (CF$_3$)$_2$N—(CH$_2$)$_r$—, B stands for a single bond, O, NH, NR, CH$_2$, C(O)—O, C(O), S, CH$_2$—O, O—C(O), N—C(O), C(O)—N, O—C(O)—N, N—C(O)—N, O—SO$_2$ or SO$_2$—O, R stands for alkyl having 1 to 4 C atoms, b stands for 0 or 1 and c stands for 0 or 1, q stands for 0 or 1, where at least one radical from b and q stands for 1, and r stands for 0, 1, 2, 3, 4 or 5, and for saturated fatty acids, whose alkylene units are represented by (CH$_2$)$_s$ in the schemes, where s can be equal to 4 to 25:

This aromatic group is introduced into the fatty acids in accordance with the scheme shown. In some cases, the respective Rf-substituted aromatic compounds are commercially available or known from the literature. Otherwise, synthetic methods are also indicated in each case. The corresponding disclosure of the said method in the cited references thus expressly also belongs to the disclosure content of the present application.

The group Rf stands for $CF_3-(CH_2)_r-$, $CF_3-(CH_2)_r-O-$, $CF_3-(CH_2)_r-S-$, $CF_3CF_2-S-$, $SF_5-(CH_2)_r-$, $[CF_3-(CH_2)_r]_2N-$, $[CF_3-(CH_2)_r]NH-$ or $(CF_3)_2N-(CH_2)_r-$, with indices as described above, and can be introduced by means of substitution reactions on aromatic compounds. If Rf is used in the following schemes, the definition given here applies, unless indicated otherwise.

The bonding of a spacer to aryl-Rf or further links via various functionalities are shown in Schemes I to VIII:

I. Etherification by Mitsunobu Reaction:

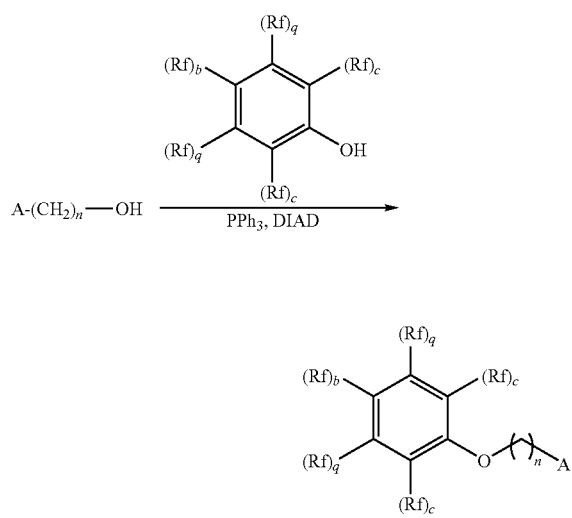

A = -CO$_2$R, where R = Me, Et
q = 0 and/or 1
b = 0 and/or 1
c = 0 and/or 1
n = 4-25

II. Linking Via Thioether or Sulfone Unit

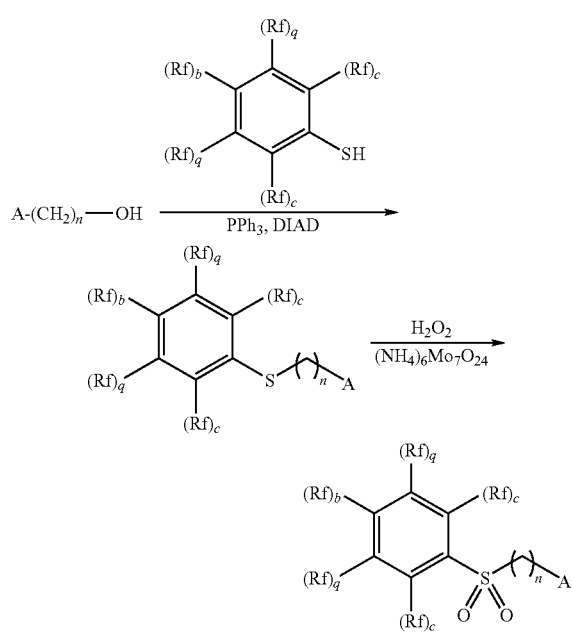

A = -CO$_2$R, where R = Me, Et
q = 0 and/or 1
b = 0 and/or 1
c = 0 and/or 1
n = 4-25

III. Amine Formation

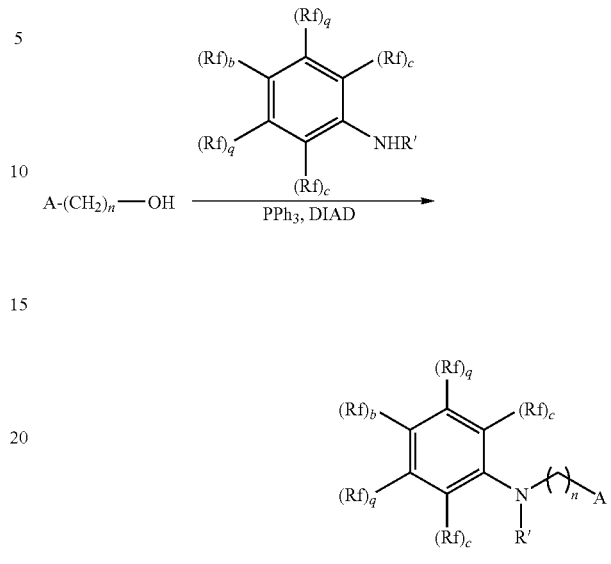

A = -CO$_2$R, where R = Me, Et
R' = H or alkyl having 1 to 4 C atoms
q = 0 and/or 1
b = 0 and/or 1
c = 0 and/or 1
n = 4-25

IV. Esterification or Amide Formation

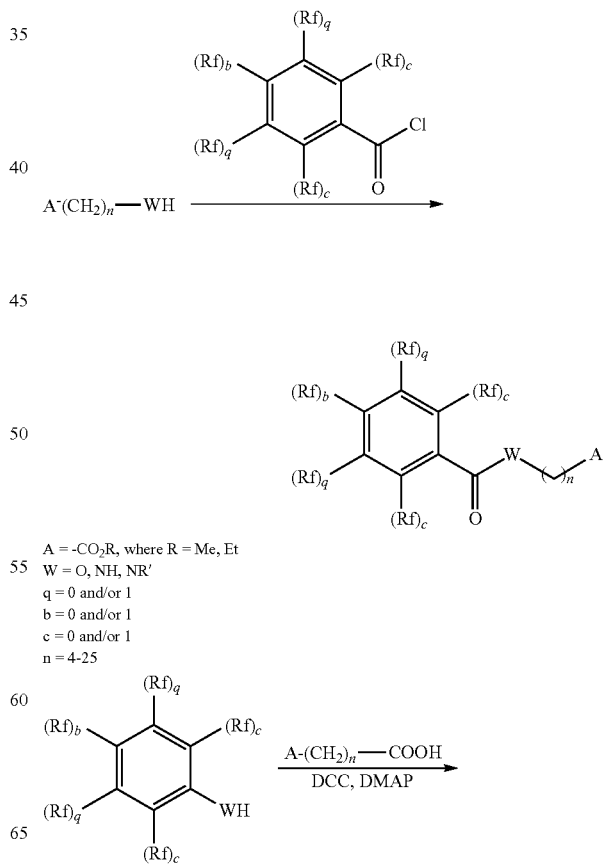

A = -CO$_2$R, where R = Me, Et
W = O, NH, NR'
q = 0 and/or 1
b = 0 and/or 1
c = 0 and/or 1
n = 4-25

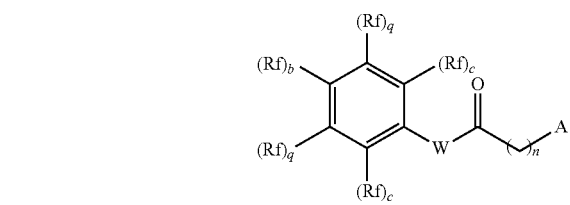

A = -CO$_2$R, where R = Me, Et
W = O, NH, NR
q = 0 and/or 1
b = 0 and/or 1
c = 0 and/or 1
n = 4-25

V. Linking Via Sulfonic Acid Esters and Amides

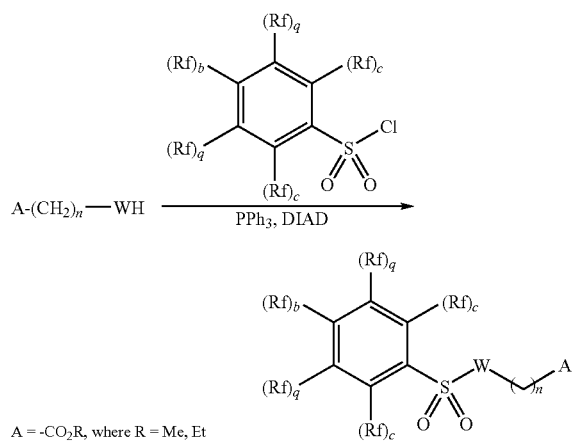

A = -CO$_2$R, where R = Me, Et
W = O, NH, NR'
R' = H or alkyl having 1 to 4 C atoms
q = 0 and/or 1
b = 0 and/or 1
c = 0 and/or 1
n = 4-25

The arylsulfonyl chloride is obtained from the corresponding aromatic compound by reaction with ClSO$_3$H.

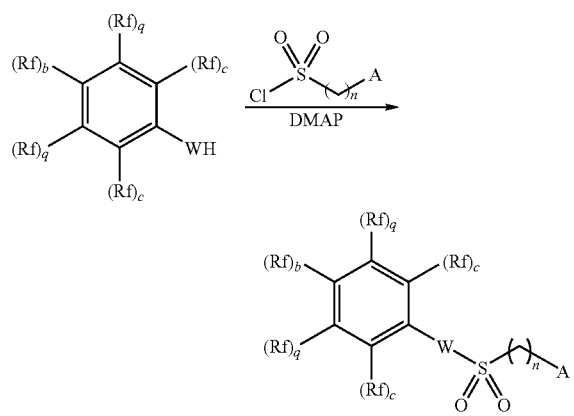

A = -CO$_2$R, where R = Me, Et
W = O, NH, NR'
R' = H or alkyl having 1 to 4 C atoms
q = 0 and/or 1
b = 0 and/or 1
c = 0 and/or 1
n = 4-25

VI. Linking Via Keto Function

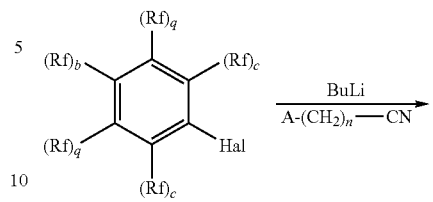

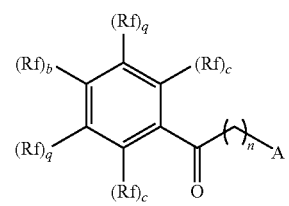

A = -CO$_2$R, where R = Me, Et
W = O, NH, NR'
Hal = Cl, Br, I
q = 0 and/or 1
b = 0 and/or 1
c = 0 and/or 1
n = 4-25

VII. Linking Via Isocyanates or Isothiocyanates

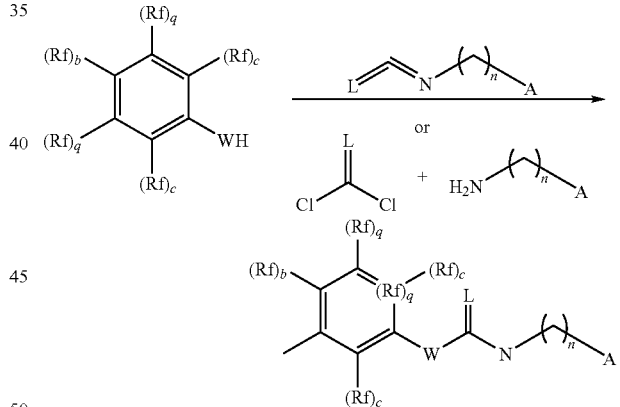

A = —CO$_2$R, where R = Me, Et
W = O, NH, NR'
L = O, S
q = 0 and/or 1
b = 0 and/or 1
c = 0 and/or 1
n = 4-25

VIII. Linking Via Heck Reaction

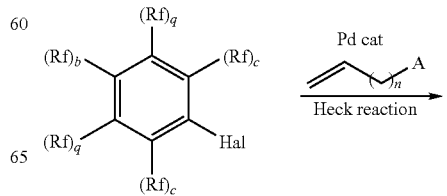

-continued

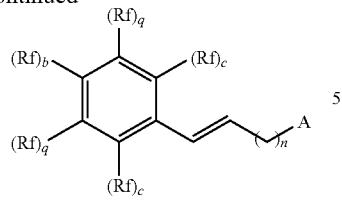

A = —CO₂R, where R = Me, Et
Hal = Cl, Br, I
q = 0 and/or 1
b = 0 and/or 1
c = 0 and/or 1
n = 4-25

The aryl building blocks with the said Rf substituents can be synthesised by the following reactions:

For CF₃ substitution: the CF₃ groups can be obtained by reaction of aromatic carboxylic acids with HF and SF₄ under superatmospheric pressure and elevated temperature, as indicated in the following scheme:

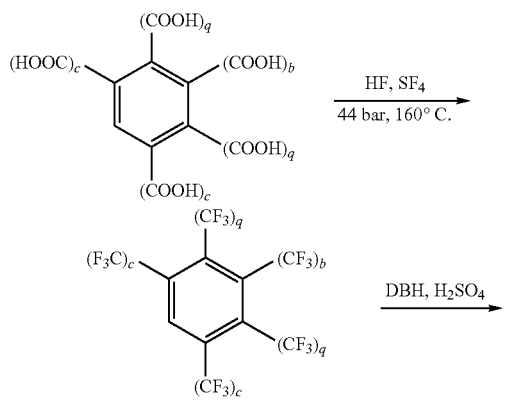

-continued

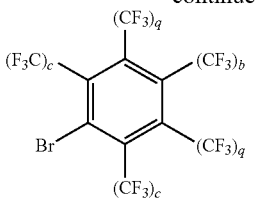

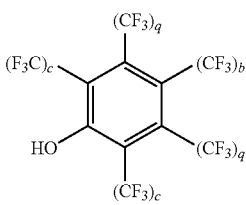

Number of substituents:
c: ortho-position (0 or at least 1)
q: meta-position (0 or at least 1)
b: para-position (0 or at least 1)
DBH = 1,3-dibromo-5,5-dimethylhydantoin Compounds of the Formula

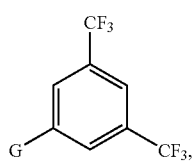

where G=—CO₂H, —CH₂NH₂, —CH₂OH, —CHO, —COCl, —CH₂Br, —CH₂CO₂H, —CH=CH₂, —CH=CHCO₂H, —C≡CCH₂OH, are commercially available.

Derivatisation for aromatic systems containing fluorinated CF₃ groups:

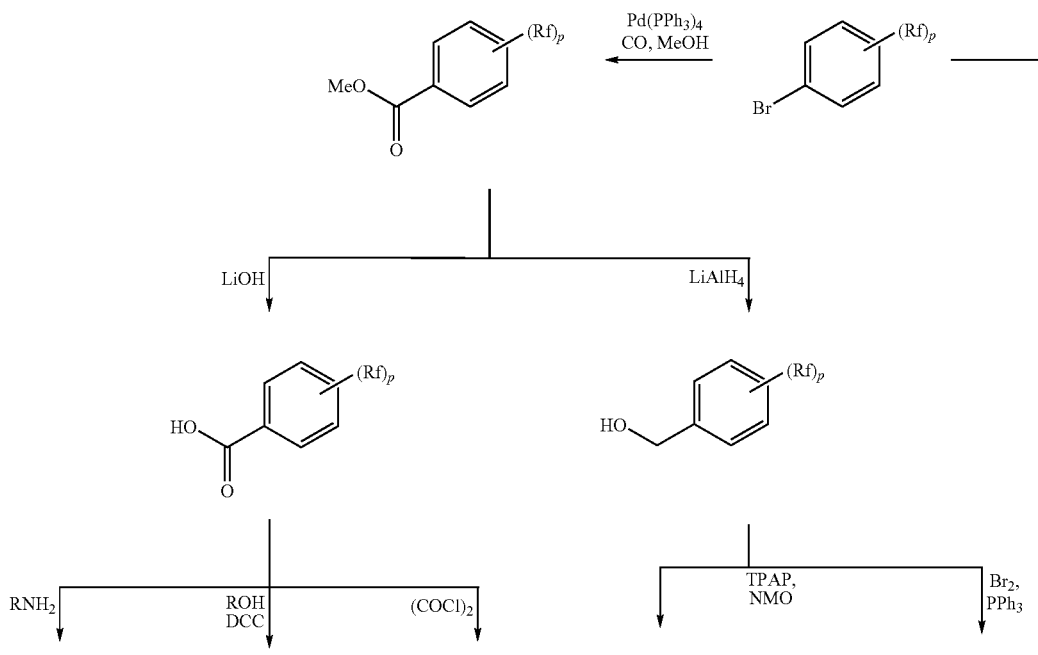

-continued
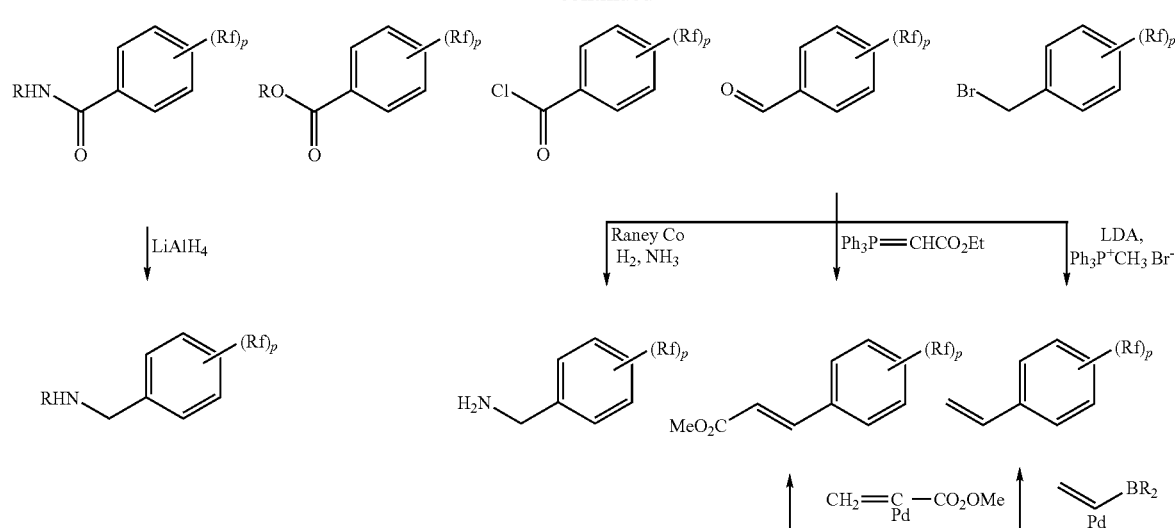
Derivatisation for aromatic systems containing 3 fluorinated $CF_3$ groups:
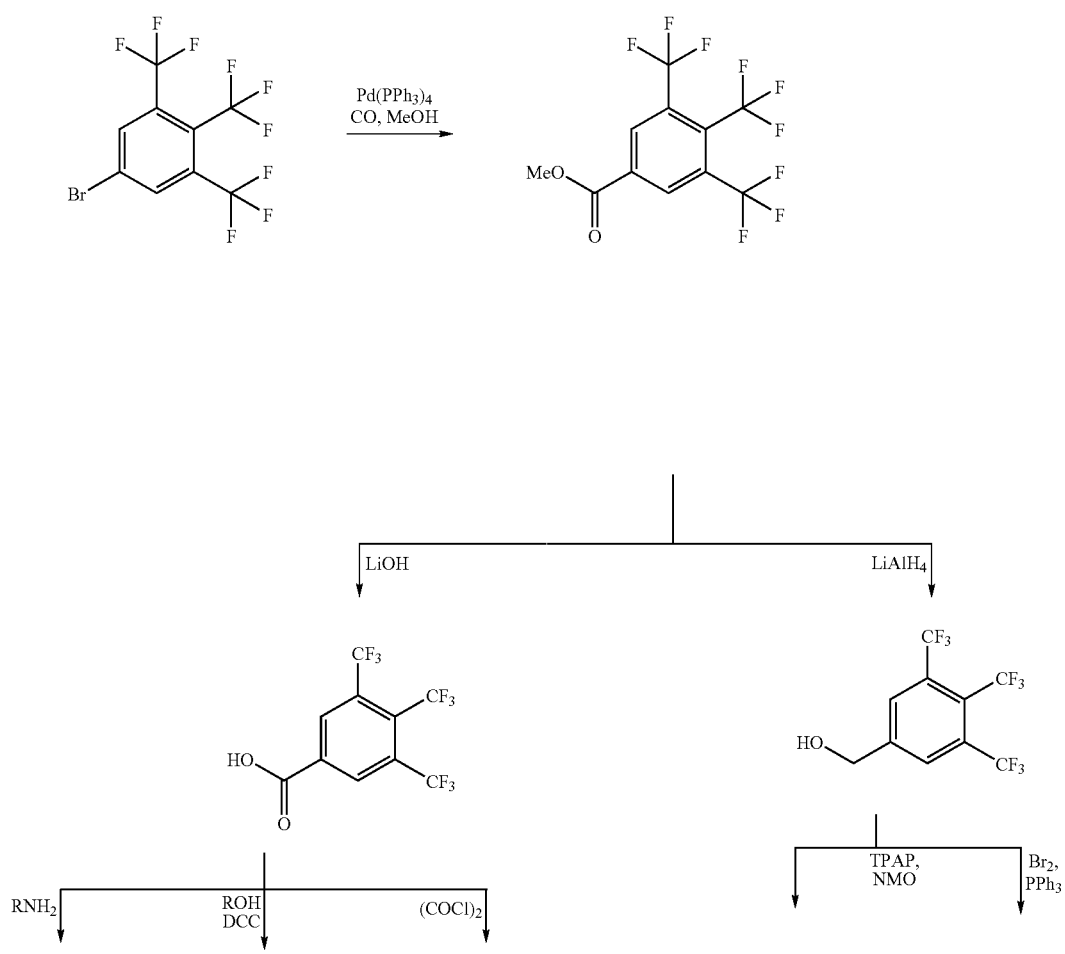

-continued

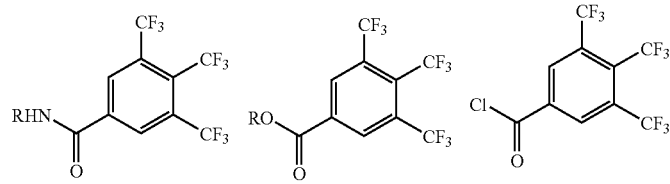
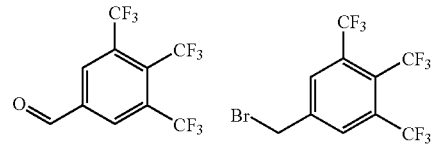

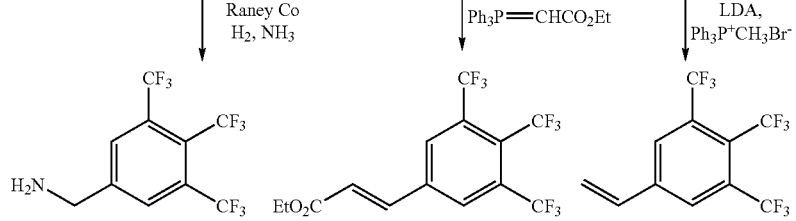

DCC: dicyclohexylcarbodiimide
TPAP: tetra-n-propylammonium perruthenate
THP: tetrahydropyranyl The following applies for SF$_5$:

The modification of commercial p-nitropentafluorosulfuranyl compounds can be carried out as described in P. Kirsch et al. Angewandte Chemie 1999, 111, 2174-2178.

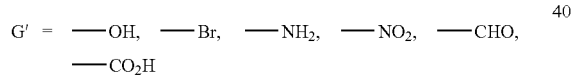

Commercial reagents are:

G' = —OH, —Br, —NH$_2$, —NO$_2$, —CHO, —CO$_2$H

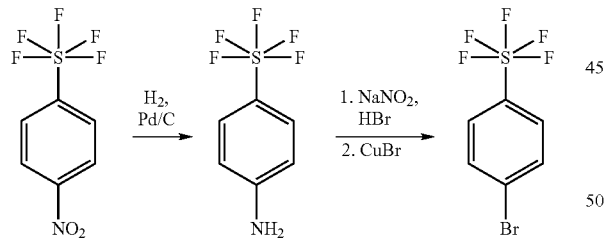

The m,m-bispentafluorosulfuranyl compounds are accessible as described in W. A. Sheppard J. Am. Chem. Soc. 1962, 84, 3064-3072 or U.S. Pat. No. 3,073,861 or U.S. Pat. No. 3,135,736:

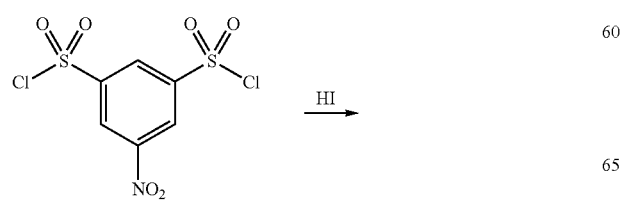

-continued

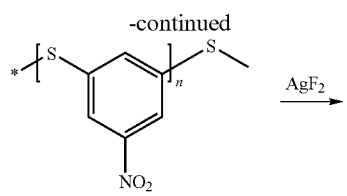

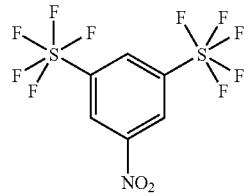

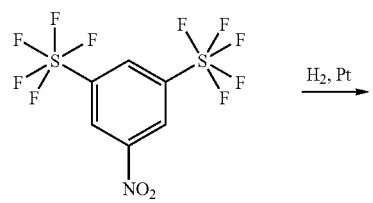

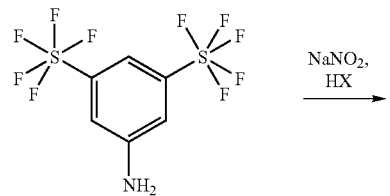

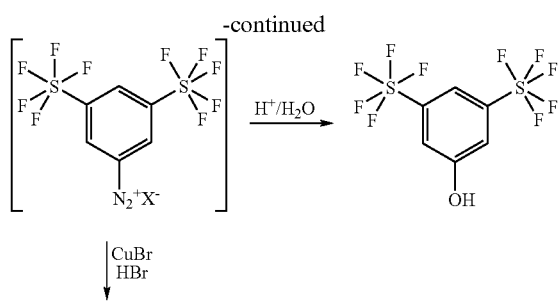

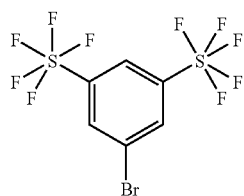

The corresponding disclosure of the said methods in the cited references thus expressly also belongs to the disclosure content of the present application.

The following applies for $F_3CS-$ or $F_5C_2S-$:

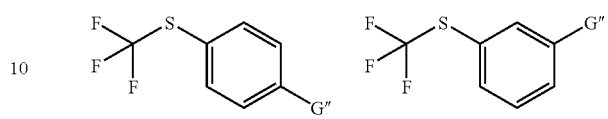

Commercial reagents are:

G''= —OH, —Br, —Cl, —NH$_2$, —NO$_2$, —N═C═O, —CHO, —CO$_2$H, —CN, —CH$_2$OH, —CH$_2$Br.

Aromatic trifluoromethyl thioethers and pentafluoroethyl thioethers are accessible by substitution of iodoaromatic compounds or etherification of thiophenols, as indicated in the following scheme:

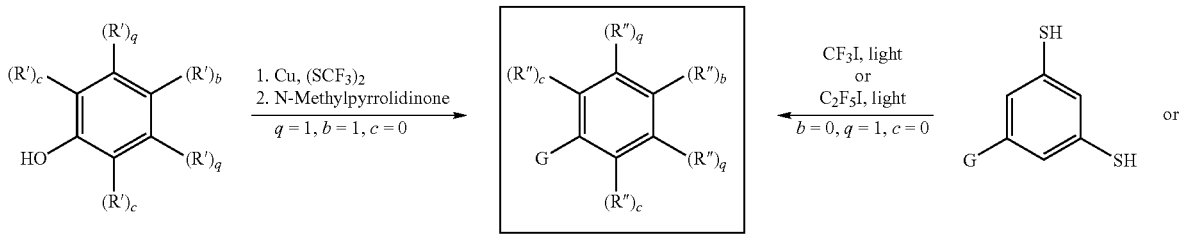

R' = —I
R'' = —SCF$_3$ or —SC$_2$F$_5$
G = —OH, —CO$_2$H
b = 0 and/or 1
c = 0 and/or 1
q = 0 and/or 1

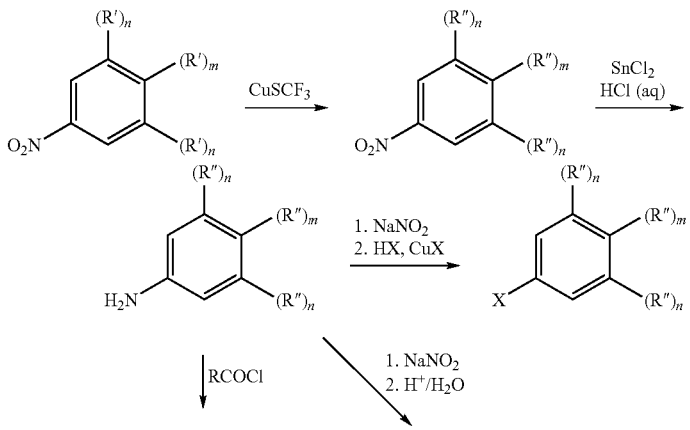

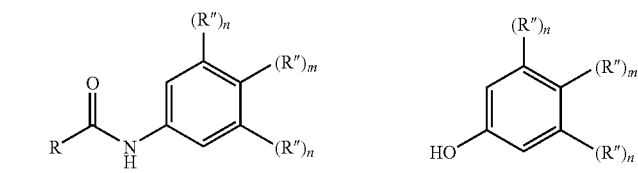

R = subst./unsubst. aryl, alkyl
R' = —I
R'' = —SCF$_3$
X = Cl, Br
m = 0 or 1
n = 0 or 1

The following applies for F₃CO:

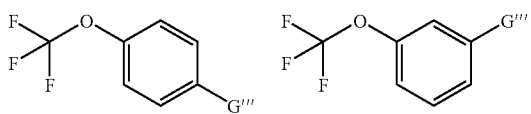

Commercial reagents or substances which are readily accessible therefrom are:

G''' = —OH, —I, —Br, —Cl, —NH$_2$, —SH, —B(OH)$_2$, —CHO, —CO$_2$H, —CO$_2$Me, —CONH$_2$, —CN, —CH$_2$OH, —CH$_2$Br, —CH$_2$CN.

Trifluoromethoxyaromatic compounds can be obtained by reaction of phenols with carbon tetrachloride and hydrogen fluoride.

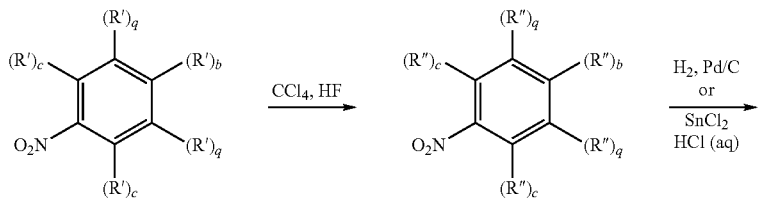

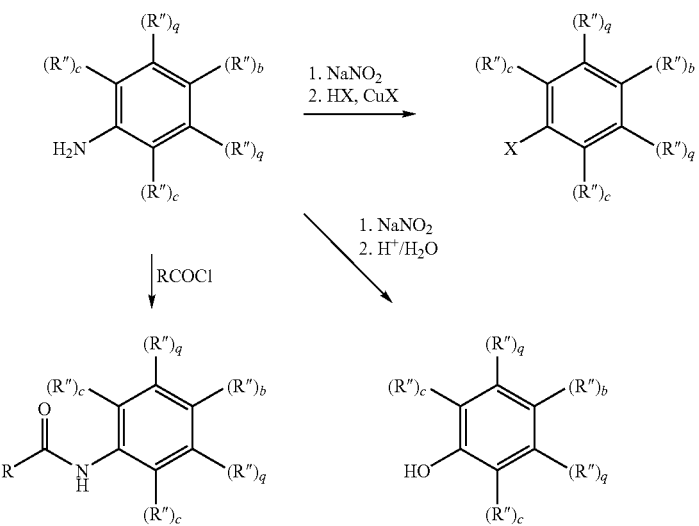

R = subst./unsubst. aryl, alkyl
R' = —I
R'' = —OCF$_3$
X = Cl, Br
c = 0 and/or 1
q = 0 and/or 1
b = 0 and/or 1

SPECIFIC EXAMPLE

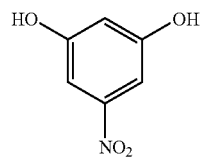

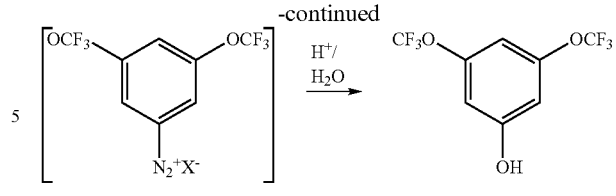

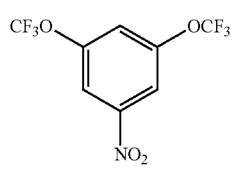

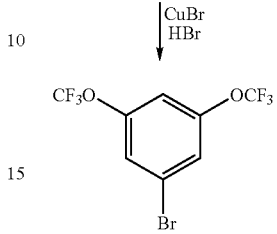

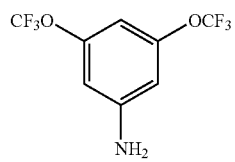

The starting material nitroresorcinol can be prepared in accordance with the following literature:

Ref. 1 Funke; Krucker; BSCFAS; Bull. Soc. Chim. Fr.; 1953; 744, 746.

Ref. 1 Grosheintz; Fischer; JACSAT; J. Am. Chem. Soc.; 70; 1948; 1476, 1478.

The following applies for $[CF_3-(CH_2)_a]_2N-$:

The amine building block $[CF_3-(CH_2)_a]_2N-$, where a stands for an integer selected from the range from 0 to 5, can be introduced with the aid of the Gabriel synthesis (Organikum: Organisch-Chemisches Grundpraktikum [Basic Practical Organic Chemistry], 16th Edn., VEB Deutscher Verlag der Wissenschaften, Berlin, 1986), followed by liberation of the primary amine by reaction with hydrazine. Subsequent alkylation of this amine using $CF_3(CH_2)_a$Hal and debenzylation gives the tertiary amino alcohol as key building block.

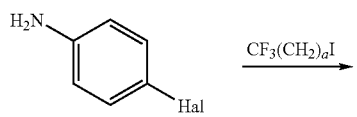

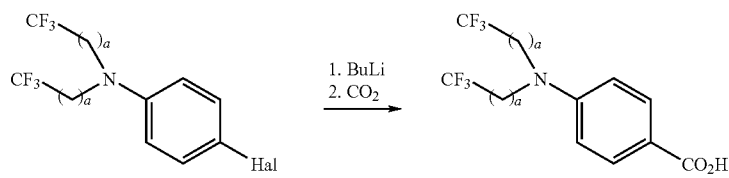

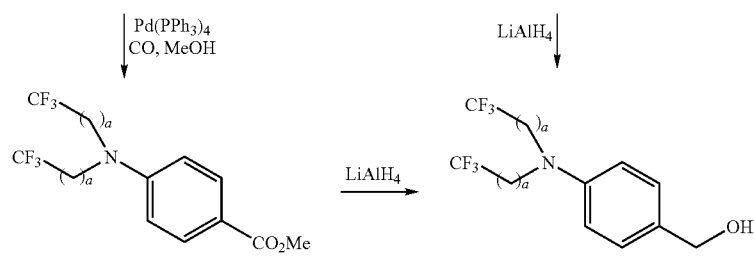

The following applies for (CF₃)₂N—:

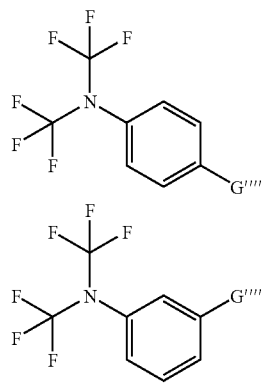

G''''

Commercial reagents or substances which are readily accessible therefrom are:

G''''=—OH, —I, —Br, —Cl, —NH₂, —NHAc, —CHO, —CO₂H, —CO₂Me, —CONH₂, —CN, —CH₂OH, —CH₂Br, —CH₂CN.

(CF₃)₂N substituents can be obtained as described by F. S. Fawcett; J. Am. Chem. Soc. 84 (No. 22) (1962) 4275-4285 starting from isocyanates by reaction with fluorophosgene and subsequent fluorination using SF₄/HF or starting from isothiocyanates by reaction with mercury difluoride and subsequent reaction with fluorophosgene, and subsequent fluorination using SF₄/HF:

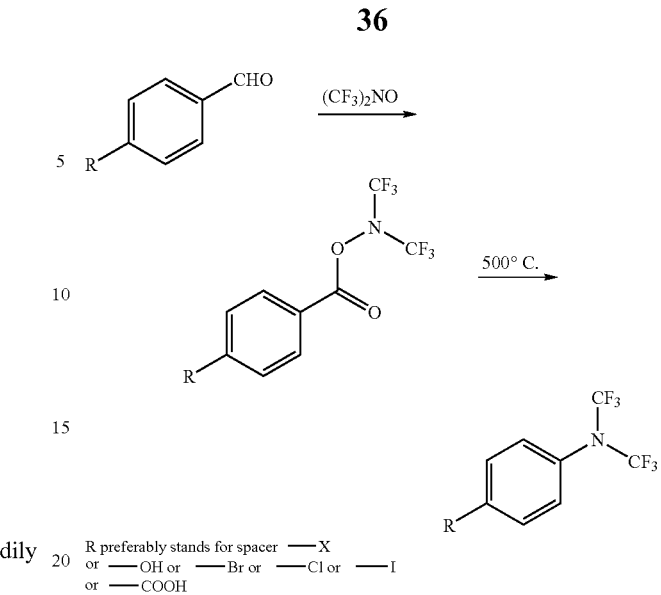

R preferably stands for spacer —X
or —OH or —Br or —Cl or —I
or —COOH

The following applies for CF₃NH—:

The end group CF₃NH— in compounds CF₃NH—R can be introduced by methods known from the literature by reaction of corresponding compounds Cl₂C=N—R with an excess of HF (corresponding syntheses are described, for example, in Petrow et al., Zh. Obshch. Khim. 29 (1959) 2169-2173 or E. Kuhle, Angew. Chem. 89 (No. 11) (1977), 797-804). Alternatively, trifluoromethyl isocyanate can also

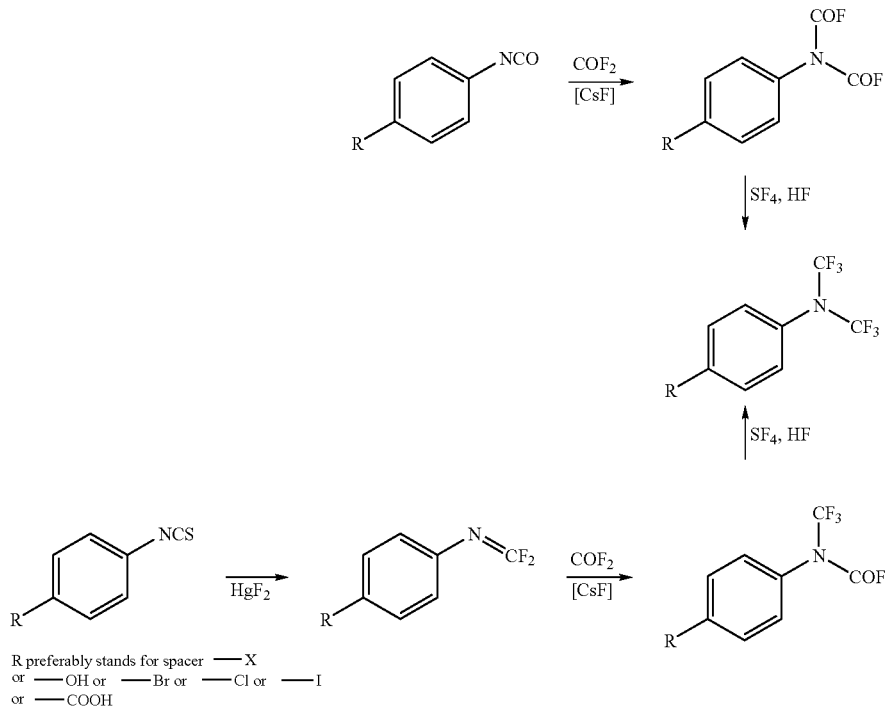

R preferably stands for spacer —X
or —OH or —Br or —Cl or —I
or —COOH

An alternative route for the preparation of the bistrifluoromethylanilines starts from aromatic aldehydes and is described in detail in R. E. Banks, J. Chem. Soc. Perkin Trans. 1 (1973) 80-82:

be reacted with an alcohol to give a compound CF₃—NHC(=O)—O—R (as described by Knunyants et al. Mendeleev chem. J. 22 (1977) 15-105 or Motornyi et al., Zh. Obshch. Khim. 29 (1959) 2157-2122). The corresponding starting materials are each obtainable by methods known from the literature, or compounds of the Cl₂C=N—R type can be obtained by reactions of compounds R—NH—CHO with chlorine and SOCl$_2$, and the radicals R of the products can be chemically modified by established methods.

The following schemes show chain extensions, which can be carried out independently of Rf:

Chain Extension by Cross-Metathesis:

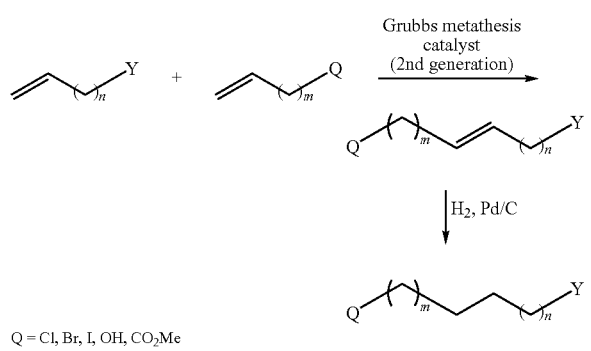

Q = Cl, Br, I, OH, CO$_2$Me

Chain Extension by Free-Radical Thiol Addition Reaction:

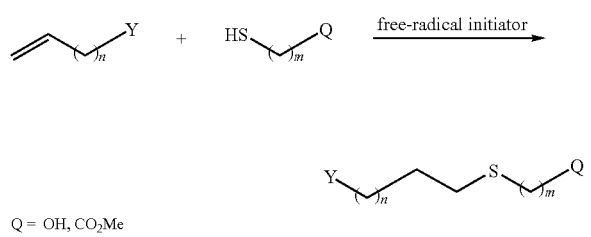

Q = OH, CO$_2$Me

Chain Extension by Wittig Reaction:

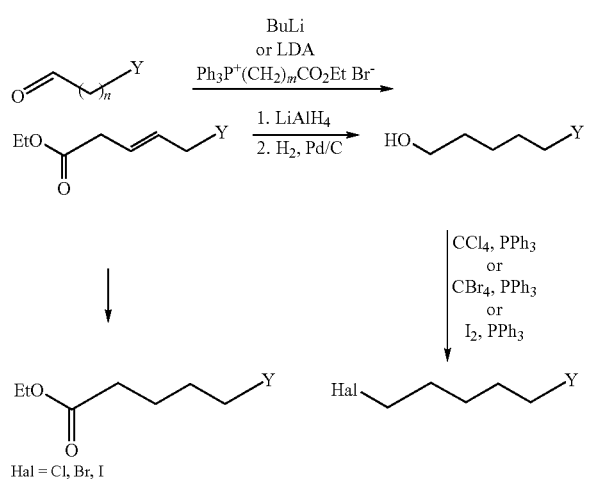

Hal = Cl, Br, I

Chain Extension by Williamson Ether Synthesis:

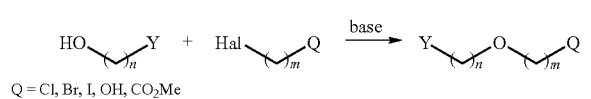

Q = Cl, Br, I, OH, CO$_2$Me

Chain Extension by Thioether Synthesis:

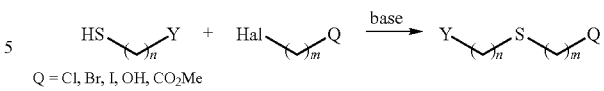

Q = Cl, Br, I, OH, CO$_2$Me

In addition, chain extensions are possible/can be carried out via ester or amide formation.

The corresponding disclosure of the said methods in the references cited here thus expressly also belongs to the disclosure content of the present application.

The choice of suitable solvents and reaction conditions presents the person skilled in the art in the case of the said reactions with absolutely no difficulties (Organikum: Organisch-Chemisches Grundpraktikum [Basic Practical Organic Chemistry], 16th Edn., VEB Deutscher Verlag der Wissenschaften, Berlin, 1986).

Advantages of the compounds according to the invention or the compositions or agents according to the invention may be, in particular:

a surface activity which may be equal or superior to the conventional hydrocarbon surfactants with respect to efficiency and/or effectiveness and/or biological and/or abiotic degradability of the substances without the formation of persistent, perfluorinated degradation products and/or good processability in formulations and/or storage stability.

The compounds which can be used in accordance with the invention as surfactants are particularly suitable for use as hydrophobicising agents or oleophobicising agents.

Areas of use are, for example, the surface modification of textiles, paper, glass, porous building materials or adsorbents. In paints, coatings, inks, photographic coatings (for photographic plates, films and papers), special coatings for semiconductor photolithography (photoresists, top antireflective coatings, bottom antireflective coatings) or other preparations for surface coating, the compounds according to the invention and the compounds to be employed in accordance with the invention can advantageously be employed with one or more of the following functions: antifogging agent, dispersant, emulsion stabiliser, antifoam, deaerating agent, antistatic, flame retardant, gloss enhancer, lubricant, pigment- or filler-compatibility enhancer, scratch-resistance enhancer, substrate adhesion enhancer, surface-adhesion reducer, skin preventer, hydrophobicising agent, oleophobicising agent, UV stabiliser, wetting agent, flow-control agent, viscosity reducer, migration inhibitor, drying accelerator. In printing inks, the compounds according to the invention and the compounds to be employed in accordance with the invention can likewise advantageously be employed and have one or more of the following functions: antifoam, deaerating agent, friction-control agent, wetting agent, flow-control agent, pigment-compatibility enhancer, print-resolution enhancer, drying accelerator.

The present invention therefore furthermore relates to the use of the compounds according to the invention or the compounds to be employed in accordance with the invention as additives in preparations for surface coating, such as printing inks, paints, coatings, photographic coatings, special coatings for semiconductor photolithography, such as photoresists, top antireflective coatings, bottom antireflective coatings, or in additive preparations for addition to corresponding preparations.

A further use according to the invention of compounds according to the invention or compounds to be employed in accordance with the invention is the use as interface promoter or emulsifier. These properties can advantageously be utilised, in particular, for the preparation of fluoropolymers by means of emulsion polymerisation.

Compounds according to the invention and compounds to be employed in accordance with the invention can be employed as foam stabiliser, in particular in preparations which are known as "fire-extinguishing foams". The invention therefore furthermore relates to the use of compounds according to the invention or compounds to be employed in accordance with the invention as foam stabiliser and/or for supporting film formation, in particular in aqueous film-forming fire-extinguishing foams, both synthetic and also protein-based, and also for alcohol-resistant formulations (AFFF and AFFF-AR, FP, FFFP and FFFP-AR fire-extinguishing foams).

Compounds according to the invention and compounds to be employed in accordance with the invention can also be used as antistatics. The antistatic action is of particular importance in the treatment of textiles, in particular clothing, carpets and carpeting, upholstery in furniture and automobiles, non-woven textile materials, leather goods, papers and cardboard articles, wood and wood-based materials, mineral substrates, such as stone, cement, concrete, plaster, ceramics (glazed and unglazed tiles, earthenware, porcelain) and glasses, and for plastics and metallic substrates. The present application relates to the corresponding use.

For metallic substrates, the present invention additionally also relates to the use of compounds according to the invention in anticorrosion agents.

The present invention furthermore also relates to the use thereof as mould-release agents in plastics processing.

In general, compounds according to the invention and compounds to be employed in accordance with the invention are suitable as protection agents against spots and soiling, stain releases, antifogging agents, lubricants, and as abrasion-resistance and mechanical wear-resistance enhancers.

Compounds according to the invention and compounds to be employed in accordance with the invention can advantageously be employed as additives in cleaning compositions and spot removers for textiles (in particular clothing, carpets and carpeting, upholstery in furniture and automobiles) and hard surfaces (in particular kitchen surfaces, sanitary installations, tiles, glass) and in polishes and waxes (in particular for furniture, flooring and automobiles) with one or more of the following functions: wetting agent, flow-control agent, hydrophobicising agent, oleophobicising agent, protection agent against spots and soiling, lubricant, antifoam, deaerating agent, drying accelerator. In the case of cleaning compositions and spot removers, the use as detergent or dirt emulsifier and dispersant is additionally also an advantageous embodiment of the present invention. The invention therefore furthermore relates to the use of compounds according to the invention or compounds to be employed in accordance with the invention in cleaning compositions and spot removers or as wetting agent, flow-control agent, hydrophobicising agent, oleophobicising agent, protection agent against spots and soiling, lubricant, antifoam, deaerating agent or drying accelerator.

The compounds according to the invention and compounds to be employed in accordance with the invention can also advantageously be used as additives in polymeric materials (plastics) with one or more of the following functions: lubricant, internal-friction reducer, UV stabiliser, hydrophobicising agent, oleophobicising agent, protection agent against spots and soiling, coupling agent for fillers, flame retardant, migration inhibitor (in particular against migration of plasticisers), antifogging agent.

On use as additives in liquid media for cleaning, etching, reactive modification and/or substance deposition on metal surfaces (in particular also electroplating and anodisation) or semiconductor surfaces (in particular for semiconductor photolithography), compounds according to the invention and compounds to be employed in accordance with the invention act as developer, stripper, edge bead remover, etching and cleaning composition, as wetting agent and/or deposited film quality enhancer. In the case of electroplating processes (in particular chrome plating), the present invention additionally also relates to the function as fume inhibitor with or without foam action.

In addition, the compounds which can be used in accordance with the invention as surfactants are suitable for washing and cleaning applications, in particular of textiles. Cleaning and polishing of hard surfaces is also a possible area of application for the compounds which can be used in accordance with the invention as surfactants. Furthermore, the compounds which can be used in accordance with the invention as surfactants can advantageously be employed in cosmetic products, such as, for example, foam baths and hair shampoos, or as emulsifiers in creams and lotions.

The compounds according to the invention and the compounds to be employed in accordance with the invention can likewise advantageously be employed as additives in hair- and bodycare products (for example hair rinses and hair conditioners), with one or more of the following functions: wetting agent, foaming agent, lubricant, antistatic, skin-grease resistance enhancer.

Compounds according to the invention and compounds to be employed in accordance with the invention act as additives in herbicides, pesticides and fungicides, with one or more of the following functions: substrate wetting agent, adjuvant, foam inhibitor, dispersant, emulsion stabiliser.

Compounds according to the invention and compounds to be employed in accordance with the invention can likewise beneficially be employed as additives in adhesives, with one or more of the following functions: wetting agent, penetration agent, substrate adhesion enhancer, antifoam. Compounds according to the invention and compounds to be employed in accordance with the invention can also serve as additives in lubricants and hydraulic fluids, with one or more of the following functions: wetting agent, corrosion inhibitor. In the case of lubricants, the use as dispersant (in particular for fluoropolymer particles) is additionally also an essential aspect.

On use as additives in putty and filling compositions, compounds according to the invention and compounds to be employed in accordance with the invention can act with one or more of the following functions: hydrophobicising agent, oleophobicising agent, protection agent against soiling, weathering-resistance enhancer, UV stabiliser, silicone bleeding inhibitor.

A further area of application for the compounds which can be used in accordance with the invention as surfactants is flotation, i.e. the recovery and separation of ores and minerals from dead rock. To this end, they are employed as additives in preparations for ore processing, in particular flotation and leaching solutions, with one or more of the following functions: wetting agent, foaming agent, foam inhibitor. A related use is also as additives in agents for the stimulation of oil wells, with one or more of the following functions: wetting agent, foaming agent, emulsifier.

In addition, they can be employed as additives in de-icing agents or icing inhibitors.

In addition, preferred compounds which can be used in accordance with the invention as surfactants can also be employed as emulsifiers or dispersion assistants in foods. Further fields of application are in metal treatment, as leather auxiliaries, construction chemistry and in crop protection.

Surfactants according to the invention are furthermore also suitable as antimicrobial active compound, in particular as reagents for antimicrobial surface modification.

The present invention relates to all uses mentioned here of compounds to be employed in accordance with the invention. The respective use of surfactants for the said purposes is known to the person skilled in the art, and consequently the use of the compounds to be employed in accordance with the invention presents no problems.

For the application, the compounds according to the invention are usually introduced into appropriately formulated preparations. The present invention likewise relates to corresponding compositions comprising at least one compound according to the invention. Such compositions preferably comprise a vehicle which is suitable for the particular application and optionally further specific active compounds and/or optionally assistants.

Preferred compositions here are paint and coating preparations, fire-extinguishing compositions, lubricants, washing and cleaning compositions, de-icers or hydrophobicising agents for textile finishing or glass treatment. In a preferred variant of the invention, the compositions are hydrophobicising agents for finishing textiles and carpets.

For the hydrophobic finishing of textiles, hydrophobicising agents based on polysiloxanes, fluorinated hydrocarbons or mixtures of aluminium or zirconium salts with paraffins are generally employed (cf. in this respect "Handbuch der Textilhilfsmittel" [Handbook of Textile Assistants], A. Chwala, V. Anger, Verlag Chemie, New York 1977, Chapter 3.24 "Phobiermittel" [Proofing Agents], pages 735 ff.). The hydrophobic finishing of textiles, in particular in the case of weather-protection clothing, serves to make these either water-resistant or waterproof. The hydrophobicising agent is applied to the fibres of the textiles, where it aligns itself in such a way that the hydrophobic parts of the molecules are perpendicular to the fibre surface. In this way, the tendency of water to spread over the entire surface is greatly reduced. The water adopts a spherical shape owing to cohesion forces and runs off the textile surface in the form of beads.

Further areas of application for compositions according to the invention are paint and coating preparations, fire-extinguishing compositions (powders and foams), lubricants, washing and cleaning compositions and de-icers.

The compositions can be prepared by methods known per se; for example by mixing the compounds according to the invention with a vehicle which is suitable for the particular application and optionally further specific active compounds and optionally assistants. The compounds to be used in accordance with the invention can be prepared by methods known per se to the person skilled in the art from the literature.

Apart from the preferred compounds mentioned in the description, the use thereof, compositions and processes, further preferred combinations of the subject-matters according to the invention are disclosed in the claims.

The disclosures in the cited references thus expressly also belong to the disclosure content of the present application.

The following examples explain the present invention in greater detail without restricting the scope of protection. In particular, the features, properties and advantages, described in the examples, of the compounds on which the particular examples are based can also be applied to other substances and compounds which are not mentioned in detail, but fall within the scope of protection, so long as nothing to the contrary is stated elsewhere. In addition, the invention can be carried out throughout the claimed range and is not restricted to the examples mentioned here.

EXAMPLES

List of Abbreviations Used:
Bn: benzyl
DBH: 1,3-dibromo-5,5-dimethylhydantoin
DCM: dichloromethane
DMAP: 4-(dimethylamino)pyridine
Me: methyl
MTB: methyl tert-butyl ether
RT room temperature (20° C.)
THF: tetrahydrofuran
PE: petroleum ether
DCC N,N'-dicyclohexylcarbodiimide
TPAP tetra-n-propylammonium perruthenate
TLC thin-layer chromatography
DIAD diisopropyl azodicarboxylate Example 1

1. Synthesis of (E)-10-pentafluorosulfanyldec-9-enecarboxylic acid

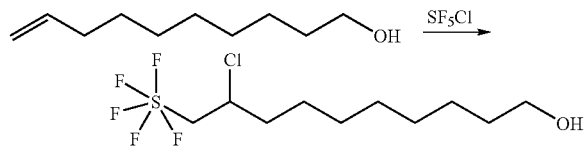

15 g of decenol are dissolved in 250 ml of DCM (dichloromethane) and cooled to −40° C. 27 g of SF$_5$Cl—previously condensed by cold trap—are passed into the apparatus as a gas. For activation, 2 ml of 1 M Et$_3$B solution are added. During passing-in of the gas, the batch becomes cloudy. The activation is repeated until the batch no longer warms when the gas is passed in. The mixture is stirred at the same temperature for a further two hours. The reaction mixture is hydrolysed by addition to ice/NaHCO$_3$ solution (saturated) and then adjusted to pH 10 using NaOH. The aqueous phase separated off is washed a further twice with MTB ether (MTB ether=methyl tert-butyl ether). The collected organic phases are extracted once with NaCl solution, dried over sodium sulfate, filtered and evaporated in a rotary evaporator. Chromatography gives the product in pure form.

Elimination:

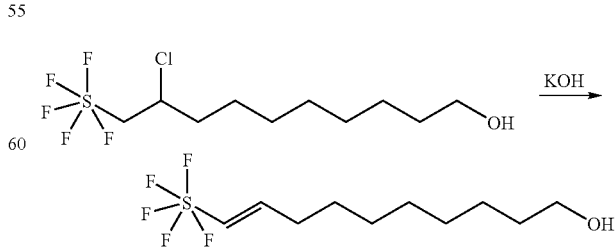

9 g of the starting material (28.2 mmol) are dissolved in 120 ml of ethanol in a 250 ml single-necked flask with reflux condenser, and KOH powder (4.75 g, 85 mmol, 3 eq) is subsequently added. The reaction mixture is stirred overnight and subsequently evaporated, and water and MTB ether are added. After the phases have been separated, the aqueous phase is extracted 3 times with MTB ether, and the collected organic phases are washed with sat. NaCl solution, dried over Na$_2$SO$_4$, filtered and freed from solvent by distillation, giving 8.3 g of yellowish liquid. The Rf value is slightly higher (less polar substance) than the starting material.

Oxidation:

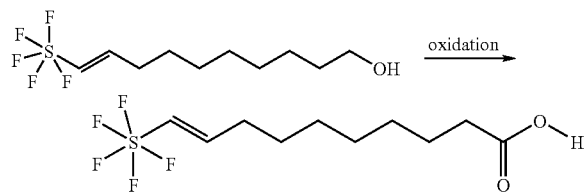

Literature: Tetrahedron Vol. 44, No. 9, p. 2636, 1988

11.3 mmol of the alcohol are dissolved in a solvent mixture comprising carbon tetrachloride (40 ml), acetonitrile (40 ml) and water (50 ml), sodium metaperiodate (5.44 g, 25.4 mmol, 2.25 eq) and ruthenium(III) chloride (234 mg, 1.13 mmol, 0.1 eq) are then added, and the reaction mixture is stirred at 22° C.-26° C. (RT) for 3 hours. 50 ml of dichloromethane are then added to the reaction mixture, the phases are separated, and the aqueous phase is extracted a further twice with 50 ml of dichloromethane each time. The combined dichloromethane solutions are dried using sodium sulfate and filtered, and the solvent is removed by distillation. The product is obtained as an oily residue.

2. Synthesis of N-methylhexanolamide

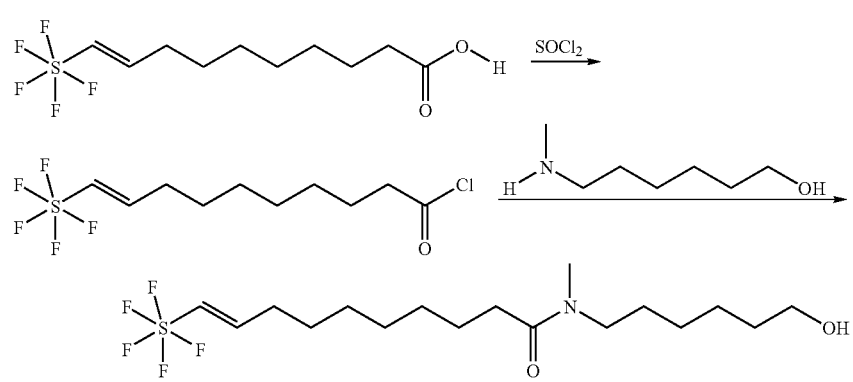

30 g of (E)-10-pentafluorosulfanyldec-9-enecarboxylic acid are initially introduced in 100 g of toluene, and 24 g of SOCl$_2$ are added. The reaction mixture is warmed to 70° C., and the excess of SOCl$_2$ and solvent is removed by distillation. The resultant acid chloride is employed without further purification in the subsequent acylation.

For the acylation, 13 g of methylaminohexanol are dissolved in 150 g of THF, and 32 g of the acid chloride and 10 g of triethylamine are added. When the reaction is complete, the product is isolated and purified by conventional laboratory methods.

Example 2

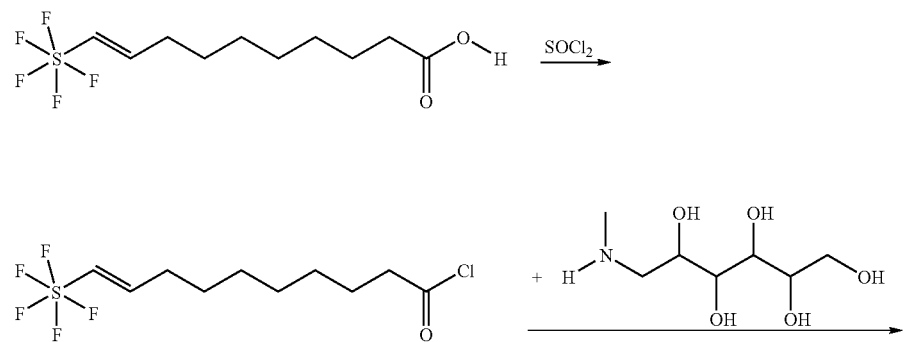

-continued

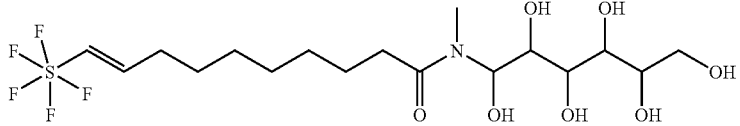

For the acylation, 20 g of N-methylglucosamine are dissolved in 150 g of THF, and 32 g of (E)-10-pentafluorosulfanyldec-9-enecarbonyl chloride, prepared analogously to Example 1, and 10 g of triethylamine are added. When the reaction is complete, the product is isolated and purified by conventional laboratory methods.

Example 3

Synthesis of methyl 7-(3,3,3-trifluoropropoxy)heptanoate

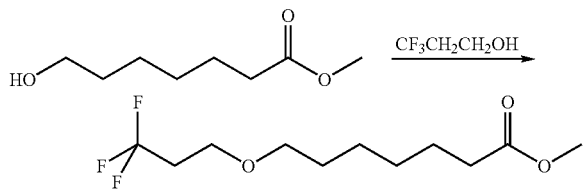

Description of the Experiment 3,3,3-Trifluoropropanol (10 ml, 110 mmol), methyl 7-hydroxyheptanoate (133 mmol, 1.2 eq), triphenylphosphine (35 g, 133 mmol, 1.2 eq) are initially introduced in 37 ml of THF in a round-bottomed flask and introduced into an ultrasound bath for a few minutes in order to mix the substances. During the exposure to ultrasound, DIAD (26.5 ml, 133 mmol, 1.2 eq) is very slowly added dropwise (temperature rises), and the reaction mixture is left under ultrasound for 15 min. A TLC sample is taken and subsequently left in the ultrasound bath for a further 2 hours.

The solvent is removed in a rotary evaporator. 90 ml of cold MTB ether are subsequently added, during which triphenylphosphine oxide precipitates out. The solid is filtered off with suction, and the solution is stored in a refrigerator over the weekend in order that the remainder also precipitates. The remaining solid is filtered off with suction, and the residue is washed with MTB. The product solution is evaporated in a rotary evaporator and purified by column chromatography.

Example 4

Synthesis of 7-(3,3,3-trifluoropropoxy)heptanoic acid

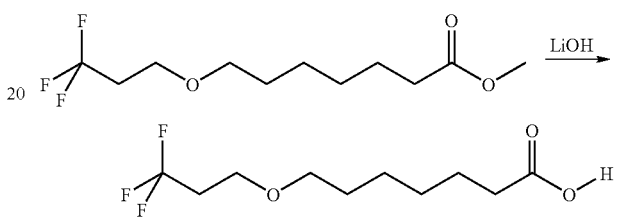

Methyl 7-(3,3,3-trifluoropropoxy)heptanoate (50 mmol) is dissolved in 500 ml of THF in a round-bottomed flask, and solid lithium hydroxide (65 mmol, 1.3 eq) is added in portions at RT. The mixture is stirred at RT for 1 hr, and 100 ml of water and 200 ml of MTB ether are subsequently added. The mixture is acidified to pH 1 using aqueous HCl, the phases are separated, and the aqueous phase is extracted a number of times with MTB. The combined organic phases are dried over sodium sulfate and evaporated in a rotary evaporator. The carboxylic acid formed in this way is employed directly in the subsequent step.

Example 5

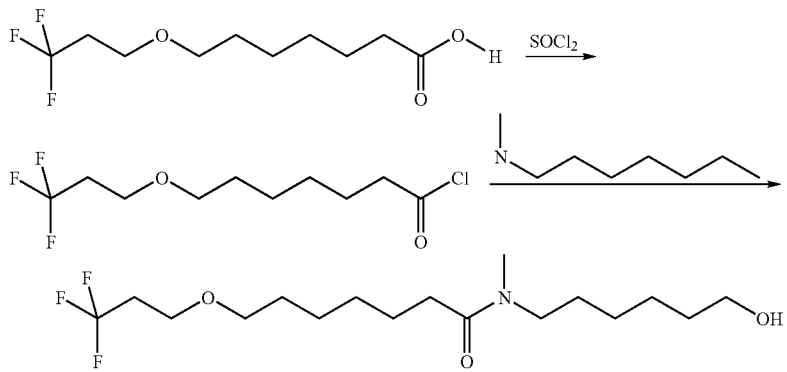

Analogously to Example 1, firstly 24 g of 7-(3,3,3-trifluoropropoxy)heptanoic acid are initially introduced in 100 g of toluene and reacted with 24 g of $SOCl_2$, and the acid chloride formed is acylated using 13 g of methylaminohexanol in 80 ml of THF and in the presence of triethylamine.

Example 6

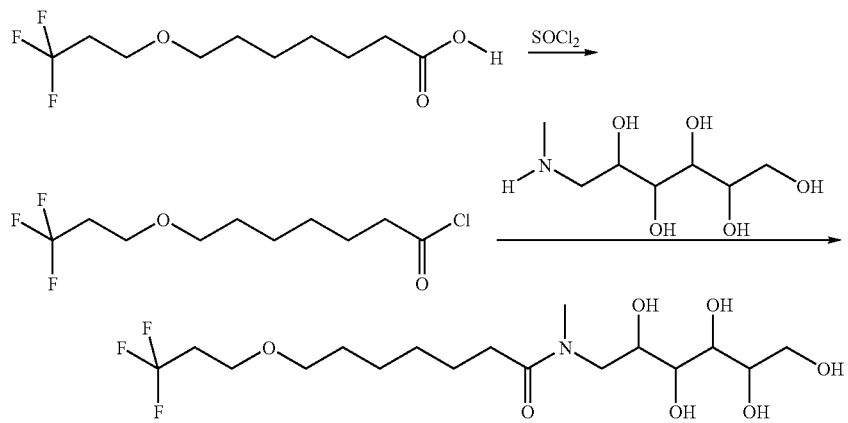

For the acylation, 20 g of N-methylglucosamine are dissolved in 150 g of THF, and 26 g of 7-(3,3,3-trifluoropropoxy)heptanoyl chloride, prepared analogously to Example 2, and 10 g of triethylamine are added. When the reaction is complete, the product is isolated and purified by conventional laboratory methods.

Example 7

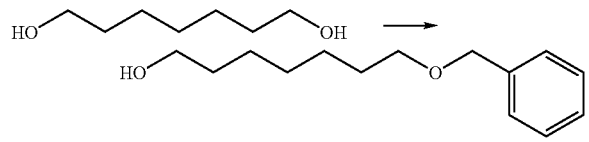

Sodium hydride (92 g, 2.3 mol, 1.36 eq) is suspended in 1200 ml of THF and cooled to 0° C. Heptane-1,7-diol (224 g, 1.7 mol) dissolved in 400 ml of THF is added dropwise to this suspension (note: evolution of $H_2$). The reaction mixture is warmed to room temperature and stirred for a further 3 hrs. Benzyl bromide (251.3 ml, 2.11 mol, 1.25 eq) and tetrabutylammonium iodide (32 g, 85 mmol, 0.05 eq) are subsequently added, and the mixture is stirred overnight (9 hrs).

For work-up, the reaction mixture is quenched using 1200 ml of ice-water, the organic phase is separated off, the aqueous phase is extracted twice with MTB ether, and the combined organic extracts are washed with saturated NaCl solution. The organic phase is dried and evaporated in a rotary evaporator, giving the crude product, which is purified over silica gel.

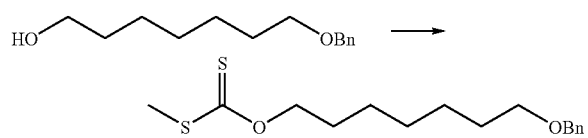

200 ml of THF and 10.15 g of NaH (253 mmol, 1.2 eq) are initially introduced into a 1 l four-necked glass apparatus which has been flushed with nitrogen, and cooled to −25° C. with stirring.

7-Benzyloxyheptan-1-ol (211 mmol, 1 eq) is mixed with 100 ml of THF and added dropwise over the course of 30 min (rinsed with 50 ml of THF), during which the internal temperature is kept at 0-5° C. The reaction mixture is then warmed to RT over the course of 30 min.

The mixture is stirred at RT for a further 120 min and subsequently cooled to −25° C. Carbon disulfide (32.1 g; 421.6 mmol; 2 eq) is added dropwise over the course of 10 min, during which the reaction mixture warms to 0° C.

The mixture is stirred at 0° C. for a further 2.5 h. The colour of the reaction mixture changes from pale-brown to brown.

For the addition of methyl iodide, the mixture is re-cooled to −20° C., and MeI (35.9 g; 253 mmol; 1.2 eq) is subsequently added dropwise over the course of 5 min (strong evolution of heat: counter-cooled at −78° C.). The reaction mixture is slowly warmed to RT and stirred at this temperature for a further 24 hrs.

For work-up, the batch is then quenched using about 10% $NH_4Cl$ solution (200 ml).

The phases are separated. The water phase is washed twice with 100 ml of MTB ether. The organic phases are combined and subsequently washed once with 100 ml of about 10% saturated NaCl solution, and the phases are separated and dried using $Na_2SO_4$, filtered and evaporated to dryness in a rotary evaporator.

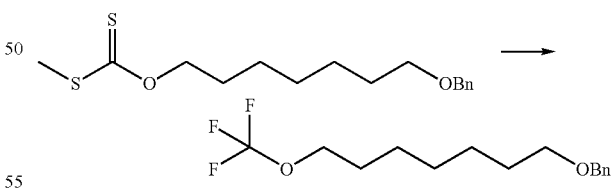

$(HF)_9$/Py (200 ml, 7.14 mol, 30 eq) and subsequently methyl xanthogenate (238 mmol) in 400 ml of DCM are added successively at −78° C. to a suspension of DBH (211 g, 738 mmol, 3.1 eq) in 1000 ml of DCM. The reaction mixture is stirred at −78° C. for a further 1 hr and slowly warmed overnight with stirring (temperature in the morning 2° C.).

The reaction mixture is warmed to 19° C. and subsequently stirred at this temperature for about 1 hour.

It is subsequently re-cooled for hydrolysis.

640 ml of $NaHSO_3$ solution and 600 ml of 47% KOH are initially introduced in a 4 l four-necked flask and cooled to 0°

C. The reaction mixture is subsequently sucked into the four-necked flask with the aid of a vacuum.

The entire mixture is made in portions. The maximum temperature should be 20° C.

The dark-red reaction solution becomes a yellowish suspension. Sufficient 47% KOH in 400 ml of demineralised water is added to this suspension until a pH of 7 has been reached. The suspension becomes thinner and thinner.

The phases are separated, and the aqueous phase is extracted twice with MTB ether. The collected organic phases are washed once with a sodium chloride solution, dried over sodium sulfate and subsequently evaporated. The crude product is stirred with active carbon and purified by column chromatography in petroleum ether.

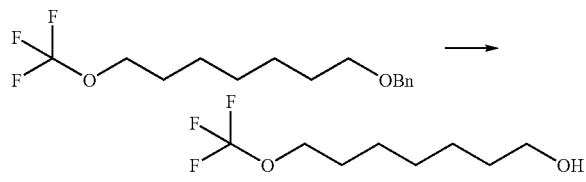

The benzyl ether (150 mmol) is taken up in ethanol (1000 ml), and 5% palladium (0.1 eq) on active carbon is added. After application of a hydrogen atmosphere (increased pressure), the progress of the reaction is investigated by TLC every hour. In order to complete the reaction, spent catalyst is filtered off, and fresh catalyst is again added. When the reaction is complete, the palladium catalyst is filtered off, and the reaction mixture is evaporated. The crude product is employed directly in the next step.

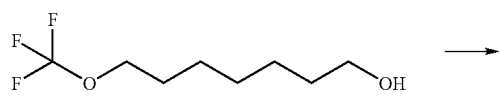

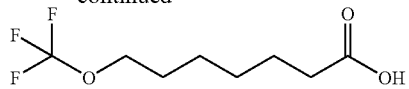

Analogously to Example 1, 22.6 mmol of the alcohol are dissolved in a solvent mixture comprising carbon tetrachloride (80 ml), acetonitrile (80 ml) and water (100 ml), sodium metaperiodate (10.88 g, 50.8 mmol, 2.25 eq) and ruthenium (III) chloride (468 mg, 2.26 mmol, 0.1 eq) are then added, and the reaction mixture is stirred at 22° C.-26° C. (RT) for 3 hours. 100 ml of dichloromethane are then added to the reaction mixture, the phases are separated, and the aqueous phase is post-extracted a further twice with 100 ml of dichloromethane each time. The combined dichloromethane solutions are dried using sodium sulfate and filtered, and the solvent is removed by distillation.

The carboxylic acid is obtained as an oily residue.

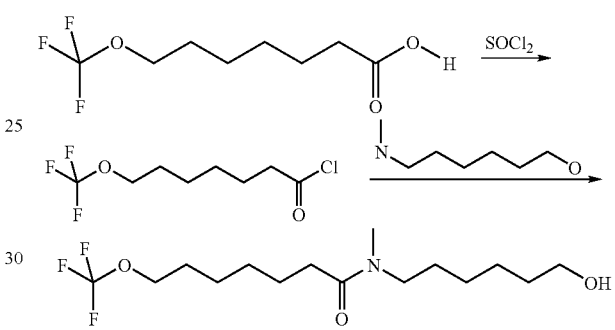

Analogously to Example 1, firstly 21 g of 7-trifluoromethoxyheptanoic acid are initially introduced in 100 g of toluene and reacted with 24 g of $SOCl_2$, and the acid chloride formed is acylated using 13 g of methylaminohexanol in THF and in the presence of 10 g of triethylamine.

Example 8

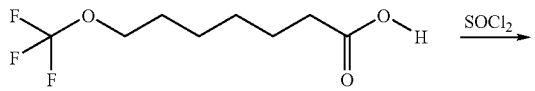

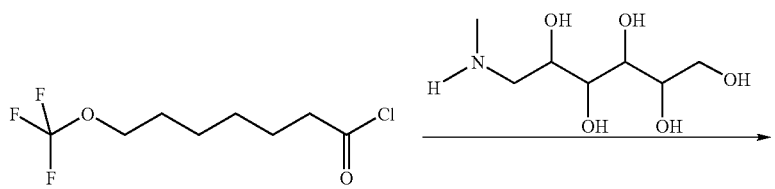

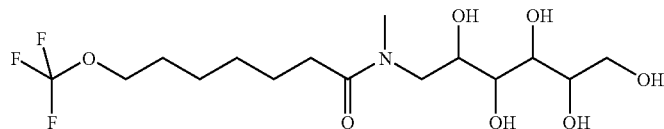

For the acylation, 20 g of N-methylglucosamine are dissolved in 150 g of THF, and 23 g of trifluoromethoxyheptanoyl chloride, prepared analogously to Example 5, and 10 g of triethylamine are added. When the reaction is complete, the product is isolated and purified by conventional laboratory methods.

Example 9

1. Synthesis of the Acid

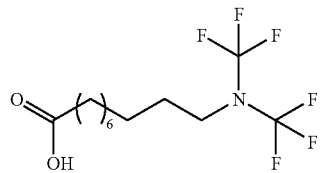

a: Preparation of the Ammonium Salt:

0.052 g (0.18 mmol) of $CF_3SO_2N(CF_3)_2$ is added at $-40°$ C. to a solution of 0.017 g (0.18 mmol) of $(CH_3)_4N^+F^-$ in 0.5 ml of dry dichloromethane. The reaction solution is warmed to room temperature and diluted with the same amount of dry acetonitrile. Removal of the solvent by distillation in a dry argon atmosphere gives 0.037 g of a colourless, highly hygroscopic material in a yield of 90.2%.

19F NMR ($CCl_3F$): $-40.8$ s; melting point: 120-125° C.

b: Preparation of the Allyl Compounds:

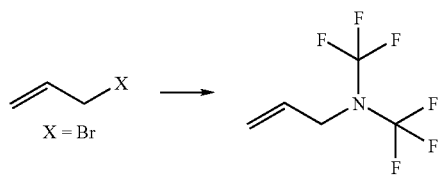

A mixture of 0.837 g (2.12 mmol) of $(CH_3)_4^+N(CF_3)_2^-$ and 0.196 g (1.62 mmol) of allyl bromide is heated under reflux under an argon atmosphere for a few hours. When the reaction is complete, the product is removed by distillation.

c: Chain Extension

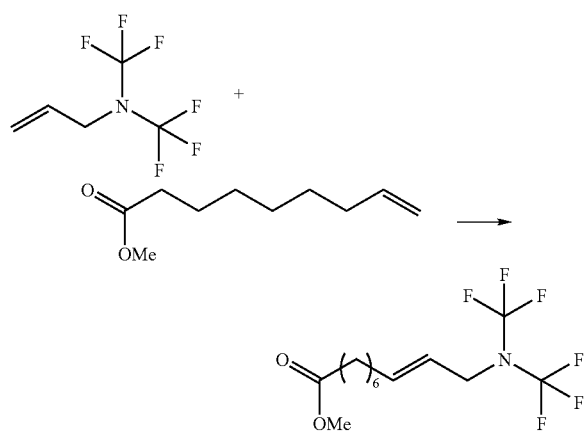

The allylamine derivative (4.2 g; 21.8 mmol) and subsequently the Grubbs II metathesis catalyst (0.9 g; 1 mmol) are added to a solution of the olefinic methyl ester (28.1 mmol) in 70 ml of dichloromethane.

The mixture is heated under reflux for 17 hrs.

The mixture is subsequently evaporated in a rotary evaporator and purified over a column. In order to remove the catalyst completely, the mixture is chromatographed again, giving the coupled product.

d: Hydrogenation of the Double Bond

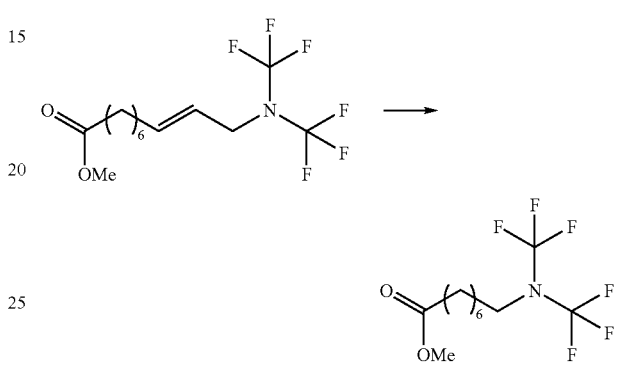

The methyl ester (27 mmol) is taken up in 250 ml of THF, and 5% palladium on active carbon (10 mol %) is added. After application of a hydrogen atmosphere (increased pressure), the reaction mixture is stirred for 3 hrs. and worked up when the reaction is complete. To this end, the catalyst is filtered off under a protective-gas atmosphere, and the solution is evaporated in a rotary evaporator.

The product can be employed directly in the subsequent step.

e: Preparation of the Acid

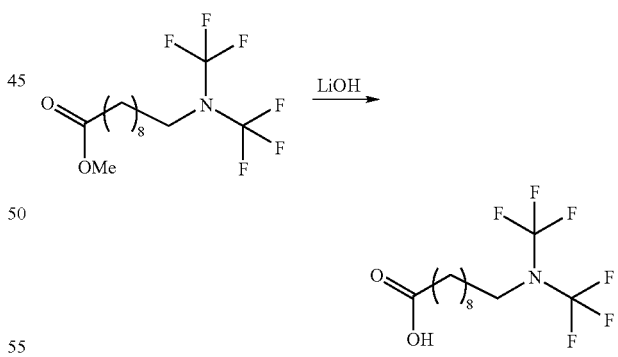

Analogously to Example 4, 10 mmol of the methyl ester are dissolved in 100 ml of THF, and solid lithium hydroxide (13 mmol, 1.3 eq) is added in portions at RT. The mixture is stirred at RT for 1 hr, and 40 ml of water and 100 ml of MTB ether are subsequently added. The mixture is acidified to pH 1 using aqueous HCl, the phases are separated, and the aqueous phase is extracted a number of times with MTB. The combined organic phases are dried over sodium sulfate and evaporated in a rotary evaporator. The carboxylic acid formed in this way is employed directly in the subsequent step.

2. Acylation

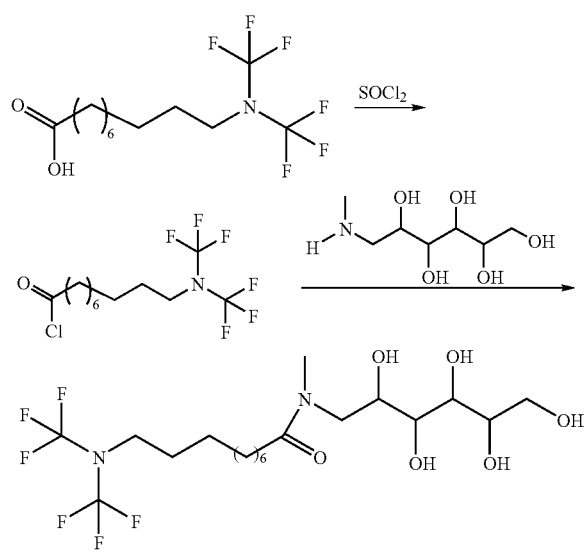

Analogously to Example 1, firstly 0.1 mol of the carboxylic acid from step 1 are initially introduced in 100 g of toluene and reacted with 24 g of SOCl$_2$, and the acid chloride formed is acylated using 13 g of methylaminohexanol in THF and in the presence of 10 g of triethylamine.

Example 10

Determination of the Biochemical Degradability

The biochemical degradability of the compounds is determined by the Zahn-Wellens test corresponding to the European Commission publication: Classification, Packaging and Labelling of Dangerous Substances in the European Union, Part II—Testing Methods, Annex V—Methods for the Determination of Physico-Chemical Properties, Toxicity and Ecotoxicity, Part B, Biochemical Degradability—Zahn-Wellens Test (C.9.), January 1997, pages 353-357.

| | |
|---|---|
| Batch volume: | 1.5 l |
| Activated sludge concentration: | 1 g of solids/l |
| Origin of the sludge: | treatment plant of Merck KGaA; Darmstadt (not adapted) |
| Amount of test substances used: | about 100 to 200 mg/l as DOC |
| Aeration: | with purified air |
| Work-up of the samples: | filtration (medium-hard filter) |
| Determination of the DOC: | by the difference method using a Dimatec instrument |

Further details on the method are given in the above publication and also the OECD Guideline for the testing of chemicals, section 3, degradation and accumulation, method 302 B, page 1-8, adopted: Jul. 17, 1992, the contents of which in this respect expressly belong to the disclosure content of the present application.

In addition, besides the degradation of the compound per se in the test, the degradation of the fluorine-containing groups is also observed via a fluoride determination:

| | |
|---|---|
| Method: | ion chromatography |
| Instrument: | Dionex 120 |
| Detector type: | conductivity detector |
| Column: | AS9HC |
| Eluent: | sodium carbonate solution, 9 mmol/l |
| Flow rate: | 1 ml/min |
| Literature: | EN ISO 10304-2 |

Example 11

Determination of the Surface Tension

| | |
|---|---|
| Instrument: | Krüss tensiometer (model K12) |
| Temperature of the measurement solutions: | 20° C. |
| Measurement module employed: | ring |
| Concentration of the measurement solutions: | about 0.5 to 3.0 g/l in deionised water |

Further details on the method are given in the European Commission publication: Classification, Packaging and Labelling of Dangerous Substances in the European Union, Part II—Testing Methods, Annex V—Methods for the Determination of Physico-Chemical Properties, Toxicity and Ecotoxicity, Part A, Surface Tension (A.5), January 1997, pages 51-57, and also the OECD Guideline for the testing of chemicals, section, physical-chemical properties, method 115, page 1-7, adopted: Jul. 27, 1995, the contents of which in this respect expressly belong to the disclosure content of the present application.

The invention claimed is:

1. A fatty acid alkanolamide or polyolamide compound containing at least one group Y in the terminal position to the amide function, which compound is of formula I

wherein

R$^1$ denotes H, alkyl having 1 to 4 C atoms or hydroxyalkyl having 2 to 4 C atoms, R$^2$ denotes a fatty acid radical containing at least one group Y, and A denotes —CH$_2$—(CHOH)$_n$—CH$_2$—OH, —(CH$_2$)$_m$—OH, —(CH$_2$CH$_2$O)$_p$—H, —(CH$_2$CH$_2$CH$_2$O)$_p$—H, or —(CH$_2$CH$_2$CH$_2$CH$_2$O)$_p$—H, wherein ethyleneoxy, propyleneoxy and/or butyleneoxy units may also occur in mixed form in the chain, n denotes 3, 4 or 5, m denotes 1 to 20, and p denotes 1 to 9, Y stands for $CF_3—(CH_2)_a—O—$, $SF_5—$, $CF_3—(CH_2)_a—S—$, $CF_3CF_2S—$, $[CF_3—(CH_2)_a]_2N—$, $[CF_3—(CH_2)_a]NH—$, or

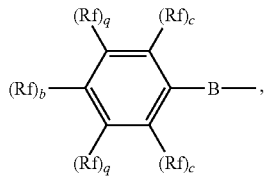

a stands for an integer from 0 to 5,
Rf stands for $CF_3—(CH_2)_r—$, $CF_3—(CH_2)_r—O—$, $CF_3—(CH_2)_r—S—$, $CF_3CF_2—S—$, $SF_5—(CH_2)_r—$, $[CF_3—(CH_2)_r]_2N—$, $[CF_3—(CH_2)_r]NH—$ or $(CF_3)_2N—(CH_2)_r—$,
B stands for a single bond, O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O,
R stands for alkyl having 1 to 4 C atoms,
b stands for 0 or 1,
c stands for 0 or 1,
q stands for 0 or 1, and
r stands for 0, 1, 2, 3, 4 or 5,
where at least one of b and q stands for 1.

2. A compound according to claim 1, wherein the fatty acid radical may be saturated or unsaturated with 4 to 25 C atoms.

3. A compound according to claim 1, wherein
A denotes —$CH_2$—(CHOH)$_n$—$CH_2$—OH, where n=3, 4 or 5.

4. A compound according to claim 1, wherein
A denotes —$(CH_2)_m$—OH, where m=1 to 20.

5. A compound according to claim 1, wherein
A denotes —$(CH_2CH_2O)_p$—H, or —$(CH_2CH_2CH_2O)_p$—H, where p=1 to 9, where the ethyleneoxy or propyleneoxy units may also occur in mixed form in the chain.

6. A compound according to claim 1, wherein
Y denotes $CF_3—(CH_2)_a—O—$, where a=0, 1, 2, 3, 4 or 5.

7. A compound according to claim 1, wherein
Y denotes $SF_5$.

8. A compound according to claim 1, wherein
Y denotes $CF_3—(CH_2)_a—S—$, where a=0, 1, 2, 3, 4 or 5.

9. A compound according to claim 1, wherein
Y denotes $CF_3—CF_2—S—$.

10. A compound according to claim 1, wherein
Y denotes $[CF_3—(CH_2)_a]_2N—$, where a=0, 1, 2, 3, 4 or 5.

11. A compound according to claim 1, wherein
Y denotes $[CF_3—(CH_2)_a]NH—$, where a=0, 1, 2, 3, 4 or 5.

12. A compound according to claim 1, wherein
Y denotes

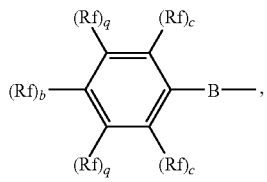

Rf stands for $CF_3—(CH_2)_r—$, $CF_3—(CH_2)_r—O—$, $CF_3—(CH_2)_r—S—$, $CF_3CF_2—S—$, $SF_5—(CH_2)_r—$, $[CF_3—(CH_2)_r]_2N—$, $[CF_3—(CH_2)_r]NH—$ or $(CF_3)_2N—(CH_2)_r—$, B stands for a single bond, O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O,
R stands for alkyl having 1 to 4 C atoms,
b stands for 0 or 1,
c stands for 0 or 1,
q stands for 0 or 1, and
r stands for 0, 1, 2, 3, 4 or 5,
where at least one of b and q stands for 1.

13. A process for preparing a compound according claim 1, comprising reacting a fatty acid containing a group Y, or a derivative of said fatty acid with an alkanolamine or polyolamine.

14. A composition comprising a compound according to claim 1 and a vehicle which is suitable for a predetermined application.

15. A composition according to claim 14, which is a paint or coating preparation, fire-extinguishing composition, lubricant, washing or cleaning composition, de-icer or hydrobicising agent for textile finishing or glass treatment.

16. A process for preparing a composition according to claim 14, comprising mixing together a compound of formula I with a vehicle which is suitable for a predetermined application.

17. A method of achieving a surfactant effect, comprising applying a compound of claim 1 to a material for which the surfactant effect is to be achieved.

18. A method for achieving a hydrophobicising or oleophobicising effect, optionally in the surface modification of textiles, paper, glass, porous building materials or adsorbents, comprising applying a compound of claim 1 to a material for which the hydrophobicising or oleophobicising effect is to be achieved.

19. A method for achieving an antistatic effect, optionally in the treatment of textiles, optionally clothing, carpets or carpeting, upholstery in furniture or automobiles, non-woven textile materials, leather goods, papers or cardboard articles, wood or wood-based materials, mineral substrates, optionally stone, cement, concrete, plaster, ceramics, optionally glazed or unglazed tiles, earthenware, porcelain, glasses, or plastics or metallic substrates, comprising applying a compound of claim 1 to a material for which the antistatic effect is to be achieved.

20. A product selected from the group consisting of surface coating, printing inks, paints, coatings, photographic coatings, special coatings for semiconductor photolithography, photoresists, top antireflective coatings, bottom antireflective coatings, and additive preparations for addition to corresponding preparations, comprising a compound of claim 1.

21. A method for achieving a foam stabilizer effect and/or for supporting film formation, optionally in fire-extinguishing foams, comprising applying a compound of claim 1 to a material for which the foam stabilizer effect and/or for supporting film formation is to be achieved.

22. A method for achieving a interface promoter effect or emulsifier effect, optionally for the preparation of fluoropolymers, comprising applying a compound of claim 1 to a material for which the interface promoter effect or emulsifier effect is to be achieved.

23. A fatty acid alkanolamide or polyolamide compound containing at least one group Y in the terminal position to the amide function, which compound is of formula I

I wherein $R^1$ denotes H, alkyl having 1 to 4 C atoms or hydroxyalkyl having 2 to 4 C atoms, $R^2$ denotes a fatty acid radical containing at least one group Y, and A denotes —$CH_2$—$(CHOH)_n$—$CH_2$—OH, —$(CH_2)_m$—OH, —$(CH_2CH_2O)_p$—H, —$(CH_2CH_2CH_2O)_p$—H, or —$(CH_2CH_2CH_2CH_2O)_p$—H, n=3, 4 or 5,
m=1 to 20, and
p=1 to 9, Y stands for $CF_3$—$(CH_2)_a$—O—, $SF_5$—, $CF_3$—$(CH_2)_a$—S—, $CF_3CF_2S$—, $[CF_3$—$(CH_2)_a]_2N$—, $[CF_3$—$(CH_2)_a]NH$—, or

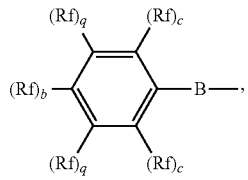

a stands for an integer from 0 to 5,
Rf stands for $CF_3$—$(CH_2)_r$—, $CF_3$—$(CH_2)_r$—O—, $CF_3$—$(CH_2)_r$—S—, $CF_3CF_2$—S—, $SF_5$—$(CH_2)_r$—, $[CF_3$—$(CH_2)_r]_2N$—, $[CF_3$—$(CH_2)_r]NH$— or $(CF_3)_2N$—$(CH_2)_r$—,
B stands for a single bond, O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O,
R stands for alkyl having 1 to 4 C atoms,
b stands for 0 or 1,
c stands for 0 or 1,
q stands for 0 or 1, and
r stands for 0, 1, 2, 3, 4 or 5,
where at least one of b and q stands for 1.

* * * * *